(12) United States Patent
Wolfram

(10) Patent No.: US 9,684,721 B2
(45) Date of Patent: *Jun. 20, 2017

(54) PERFORMING MACHINE ACTIONS IN RESPONSE TO VOICE INPUT

(71) Applicant: WOLFRAM ALPHA LLC, Champaign, IL (US)

(72) Inventor: Stephen Wolfram, Concord, MA (US)

(73) Assignee: Wolfram Alpha LLC, Champaign, IL (US)

( * ) Notice: Subject to any disclaimer, the term of this patent is extended or adjusted under 35 U.S.C. 154(b) by 93 days.

This patent is subject to a terminal disclaimer.

(21) Appl. No.: 14/629,398

(22) Filed: Feb. 23, 2015

(65) Prior Publication Data

US 2015/0169769 A1 Jun. 18, 2015

Related U.S. Application Data

(63) Continuation of application No. 14/082,581, filed on Nov. 18, 2013, now Pat. No. 8,966,439, which is a continuation of application No. 11/852,044, filed on Sep. 7, 2007, now Pat. No. 8,589,869.

(60) Provisional application No. 60/842,756, filed on Sep. 7, 2006.

(51) Int. Cl.
| | |
|---|---|
| G06F 9/44 | (2006.01) |
| G06F 7/00 | (2006.01) |
| G06F 17/00 | (2006.01) |
| G10L 15/00 | (2013.01) |
| G06F 17/30 | (2006.01) |
| G06F 17/21 | (2006.01) |
| G06F 3/01 | (2006.01) |

(Continued)

(52) U.S. Cl.
CPC ......... *G06F 17/30864* (2013.01); *G06F 3/01* (2013.01); *G06F 8/30* (2013.01); *G06F 17/215* (2013.01); *G06F 19/707* (2013.01); *G10L 15/22* (2013.01)

(58) Field of Classification Search
CPC . G06F 3/01; G06F 8/30; G06F 17/215; G06F 17/30864; G06F 19/707; G10L 15/22; G10L 15/265; G10L 17/005
USPC ............... 717/100, 104–113, 125, 136, 137; 704/231, 246–250, 257, 275; 707/706–712, 723, 769–780; 715/255, 715/256, 267
See application file for complete search history.

(56) References Cited

U.S. PATENT DOCUMENTS

| | | |
|---|---|---|
| 4,734,854 A | 3/1988 | Afshar |
| 4,740,886 A | 4/1988 | Tanifuji et al. |
| 4,841,441 A | 6/1989 | Nixon et al. |

(Continued)

FOREIGN PATENT DOCUMENTS

| | | |
|---|---|---|
| EP | 0 442 240 A2 | 8/1991 |
| WO | WO-97/40425 A2 | 10/1997 |

(Continued)

OTHER PUBLICATIONS

Adorni, et al., "Natural Language Input for Scene Generation," Proceedings of the first conference on European Chapter of the Association for Computational Linguistics, pp. 175-182 (1983).

(Continued)

*Primary Examiner* — Qing Chen

(57) ABSTRACT

In a method for determining an answer to a query expressed in an imprecise syntax, a formula for computing an answer to the query is determined. An answer is calculated using the formula, and the answer is then presented to the user.

40 Claims, 16 Drawing Sheets

(51) Int. Cl.
  *G10L 15/22* (2006.01)
  *G06F 19/00* (2011.01)

(56) References Cited

U.S. PATENT DOCUMENTS

| | | | |
|---|---|---|---|
| 4,949,253 A | 8/1990 | Chigira et al. |
| 5,038,296 A | 8/1991 | Sano |
| 5,315,710 A | 5/1994 | Kishimoto et al. |
| 5,394,509 A | 2/1995 | Winston |
| 5,448,740 A | 9/1995 | Kiri et al. |
| 5,485,601 A | 1/1996 | Ching |
| 5,499,371 A | 3/1996 | Henninger et al. |
| 5,555,367 A | 9/1996 | Premerlani et al. |
| 5,559,939 A | 9/1996 | Wada et al. |
| 5,634,024 A | 5/1997 | Yamaguchi |
| 5,640,576 A | 6/1997 | Kobayashi et al. |
| 5,696,962 A | 12/1997 | Kupiec |
| 5,768,590 A | 6/1998 | Kimura et al. |
| 5,815,713 A | 9/1998 | Sanders |
| 5,815,717 A | 9/1998 | Stack |
| 5,987,505 A | 11/1999 | Fry et al. |
| 6,038,560 A | 3/2000 | Wical |
| 6,076,051 A | 6/2000 | Messerly et al. |
| 6,084,585 A | 7/2000 | Kraft et al. |
| 6,144,989 A | 11/2000 | Hodjat et al. |
| 6,169,986 B1 | 1/2001 | Bowman et al. |
| 6,173,441 B1 | 1/2001 | Klein |
| 6,216,139 B1 | 4/2001 | Listou |
| 6,256,665 B1 | 7/2001 | Fry et al. |
| 6,275,976 B1 | 8/2001 | Scandura |
| 6,289,513 B1 | 9/2001 | Bentwich |
| 6,493,694 B1 | 12/2002 | Xu et al. |
| 6,502,236 B1 | 12/2002 | Allen et al. |
| 6,505,157 B1 | 1/2003 | Elworthy |
| 6,584,464 B1 | 6/2003 | Warthen |
| 6,589,290 B1 | 7/2003 | Maxwell et al. |
| 6,604,075 B1 | 8/2003 | Brown et al. |
| 6,675,159 B1 | 1/2004 | Lin et al. |
| 6,684,388 B1 | 1/2004 | Gupta et al. |
| 6,704,728 B1 | 3/2004 | Chang et al. |
| 6,742,162 B2 | 5/2004 | Bennett |
| 6,876,314 B1 | 4/2005 | Lin |
| 6,877,155 B1 | 4/2005 | Lindsey |
| 6,901,399 B1 | 5/2005 | Corston et al. |
| 6,973,640 B2 | 12/2005 | Little et al. |
| 6,996,801 B2 | 2/2006 | Yoneyama |
| 7,120,574 B2 | 10/2006 | Troyanova et al. |
| 7,137,100 B2 | 11/2006 | Iborra et al. |
| 7,188,067 B2 | 3/2007 | Grant et al. |
| 7,197,739 B2 | 3/2007 | Preston et al. |
| 7,222,333 B1 | 5/2007 | Mor et al. |
| 7,231,343 B1 | 6/2007 | Treadgold et al. |
| 7,263,517 B2 | 8/2007 | Sheu et al. |
| 7,269,822 B2 | 9/2007 | Gebhart et al. |
| 7,373,291 B2 | 5/2008 | Garst |
| 7,440,968 B1 | 10/2008 | Oztekin et al. |
| 7,451,135 B2 | 11/2008 | Goldman et al. |
| 7,454,701 B2 | 11/2008 | Graeber |
| 7,613,676 B2 | 11/2009 | Baisley et al. |
| 7,620,935 B2 | 11/2009 | Baisley et al. |
| 7,640,160 B2 | 12/2009 | Di Cristo et al. |
| 7,685,507 B2 | 3/2010 | Workman et al. |
| 7,747,601 B2 | 6/2010 | Cooper et al. |
| 7,747,981 B2 | 6/2010 | Gray |
| 7,844,594 B1 | 11/2010 | Holt et al. |
| 8,086,604 B2 | 12/2011 | Arrouye et al. |
| 8,091,024 B2 | 1/2012 | Graeber |
| 8,135,696 B2 | 3/2012 | Safoutin |
| 8,185,523 B2 | 5/2012 | Lu et al. |
| 8,275,617 B1 | 9/2012 | Morgan et al. |
| 8,589,869 B2 | 11/2013 | Wolfram |
| 8,788,524 B1 | 7/2014 | Wolfram et al. |
| 8,966,439 B2 | 2/2015 | Wolfram |
| 9,213,768 B1 | 12/2015 | Wolfram et al. |
| 2002/0099743 A1 | 7/2002 | Workman et al. |
| 2002/0116176 A1 | 8/2002 | Tsourikov et al. |
| 2002/0140734 A1 | 10/2002 | Bennett |
| 2002/0143810 A1 | 10/2002 | Bennett |
| 2002/0174120 A1 | 11/2002 | Zhang et al. |
| 2003/0145022 A1 | 7/2003 | Dingley |
| 2003/0191765 A1 | 10/2003 | Bargh et al. |
| 2004/0001109 A1 | 1/2004 | Blancett et al. |
| 2004/0049499 A1 | 3/2004 | Nomoto et al. |
| 2004/0088158 A1 | 5/2004 | Sheu et al. |
| 2004/0103405 A1 | 5/2004 | Vargas |
| 2004/0128649 A1 | 7/2004 | Grundy et al. |
| 2005/0005258 A1 | 1/2005 | Bhogal et al. |
| 2005/0080780 A1 | 4/2005 | Colledge et al. |
| 2005/0097464 A1 | 5/2005 | Graeber |
| 2006/0020886 A1 | 1/2006 | Agrawal et al. |
| 2006/0025987 A1 | 2/2006 | Baisley et al. |
| 2006/0026576 A1 | 2/2006 | Baisley et al. |
| 2006/0136411 A1 | 6/2006 | Meyerzon et al. |
| 2006/0190439 A1 | 8/2006 | Chowdhury et al. |
| 2006/0271908 A1 | 11/2006 | Bargh et al. |
| 2006/0276230 A1 | 12/2006 | McConnell |
| 2006/0279799 A1 | 12/2006 | Goldman |
| 2007/0022109 A1 | 1/2007 | Imielinski et al. |
| 2007/0043574 A1 | 2/2007 | Coffman et al. |
| 2007/0106657 A1 | 5/2007 | Brzeski et al. |
| 2007/0106659 A1 | 5/2007 | Lu et al. |
| 2007/0203929 A1 | 8/2007 | Bolivar |
| 2007/0208722 A1 | 9/2007 | Dettinger et al. |
| 2007/0220034 A1 | 9/2007 | Iyer et al. |
| 2008/0016040 A1 | 1/2008 | Jones et al. |
| 2008/0066052 A1 | 3/2008 | Wolfram |
| 2008/0153465 A1 | 6/2008 | Evermann et al. |
| 2008/0154611 A1 | 6/2008 | Evermann et al. |
| 2008/0154612 A1 | 6/2008 | Evermann et al. |
| 2008/0154870 A1 | 6/2008 | Evermann et al. |
| 2009/0055733 A1 | 2/2009 | Graeber |
| 2009/0171923 A1 | 7/2009 | Nash et al. |
| 2010/0004924 A1 | 1/2010 | Paez |
| 2010/0293174 A1 | 11/2010 | Bennett et al. |

FOREIGN PATENT DOCUMENTS

| | | |
|---|---|---|
| WO | WO-2006/014892 A2 | 2/2006 |
| WO | WO-2006/015006 A2 | 2/2006 |

OTHER PUBLICATIONS

"AppleScript," Wikipedia (2009).
"Area calculator," http://www.calculator.com, 2 page. (Aug. 15, 2006).
Asperti et al., "A content based mathematical search engine: Whelp," pp. 1-15 (2004).
"calculator.com," http://www.calculator.com, 2 pages (Aug. 15, 2006).
"Car Lease Calculator," http://www.calculator.com, 1 page. (Aug. 15, 2006).
"Currency Calculator," http://www.calculator.com, 1 page. (Aug. 15, 2006).
Estival et al., "Towards Ontology-Based Natural Language Processing," http://acl.ldc.upenn.edu/acl2004/nlpxml/pdf/estival-etal.pdf; 8 pages (Mar. 8, 2010). <http://acl.ldc.uoenn.edu/acl2004/nlpxml/pdf/estival-etal.pdf>.
"Fractions calculator," http://www.calculator.com, 1 page (Aug. 15, 2006).
"General Loan Calculator," http://www.calculator.com, 1 page (Aug. 15, 2006).
"Google Code," <http://code.google.com/>, pp. 1-11 (Mar. 17,2005).
"Graphing calculator," http://www.calculator.com, 1 page (Aug. 15, 2006).
"Home Equity Calculator," http://www.calculator.com, 1 page (Aug. 15, 2006).
"Home-Finance," http://www.calculator.com, 2 pages (Aug. 15, 2006).
"How Much Can I Afford Calculator," http://www.calculator.com, 1 page (Aug. 15, 2006).

(56) References Cited

OTHER PUBLICATIONS

Jones et al., "Generating Query Substitutions," ACM WWW 2006, pp. 387-396 (May 23, 2006).
Kamareddine et al., "Restoring Natural Language as a Computerised Mathematics Input Method," Proceedings of the 14th symposium on Towards Mechanized +Mathematical Assistants: 6th International Conference, pp. 280-295 (2007).
Ko, et al., "The State of the Art in End-User Software Engineering," accepted for publication in ACM Computing Surveys. pp. 1-61 (2010).
Lavrov, "Program Synthesis," Cybernetics and Systems Analysis, vol. 18, No. 6 pp. 708-715 (Nov. 1982).
"Length Adding Calculator," http://www.calculator.com, 1 page (Aug. 15, 2006).
"Love Calculator," http://www.calculator.com, 1 page (Aug. 15, 2006).
Meyers, A., "VOX—An Extensible Natural Language Processor," http://dli.iiitac.in/ijcai/IJA1-85-VOL2/PDF/026.pdf <http://dli.iiit.ac.in/iicai/!.JCAI>, 5 pages (Mar. 8, 2010).
Moore, Gregory M., "Calculator Code: Programming Code for Use within a Scientific Calculator," p. 1-29 (Fall 2005).
"Mortgage Payment Calculator," http://www.calculator.com, 1 page (Aug. 15, 2006).
"Mortgage Qualification Calculator," http://www.calculator.com, 1 page (Aug. 15, 2006).
Myers et al., "Natural Programming Languages and Environments," Communications of the ACM, vol. 47, No. 9, pp. 47-52 (Sep. 2004).
Osogami, "A Study of Input and Output Conditions for Automatic Program Generation," Memoirs of the Fukui Institute of Technology, vol. 37, pp. 273-278 (2007).
"Percent calculator," http://www.calculator.com, 1 page (Aug. 15, 2006).
"Rent versus Buy Calculator," http://www.calculator.com, 1 page (Aug. 15, 2006).
"Scientific calculator," http://www.calculator.com, 1 page (Aug. 15, 2006).
"Standard calculator," http://www.calculator.com, 1 page (Aug. 15, 2006).
Sucan, Ioan Alexandru, "A Search Engine for Mathematical Formulae," p. 1-17 (May 7, 2006).
"Temperature calculator," http://www.calculator.com, 1 page (Aug. 15, 2006).
"The Mortgage Calculator," <http://www.hughchou.org/calc/mortold.html>, pp. 1-7 (Aug. 8, 1996).
"Time Calculator," http://www.calculator.com, 1 page (Aug. 15, 2006).
Trott, Michael, "The Functions Website," the Mathematica Journal, p. 1-10 (2003).
Trott, Michael, "Mathematical Searching of the Wolfram Functions Site," The Mathematica Journal, p. 713-726 (2005).
"Unit Conversion Calculator," http://www.calculator.com, 1 page (Aug. 15, 2006).
Wang et al., "Mining Term Association Patterns from Search Logs for Effective Query Reformulation," ACM CIKM 2008, pp. 479-488 (Oct. 26, 2008).
First Office Action in U.S. Appl. No. 12/780,705, dated Jan. 31, 2012 (21 pages).
Second Office Action in U.S. Appl. No. 12/780,705, dated Aug. 16, 2012 (16 pages).
Third Office Action in U.S. Appl. No. 12/780,705, dated Jan. 2, 2014 (16 pages).
Notice of Allowance in U.S. Appl. No. 12/780,705, dated Jun. 4, 2014 (6 pages).
First Office Action in U.S. Appl. No. 12/780,685, dated Feb. 15, 2012 (26 pages).
Second Office Action in U.S. Appl. No. 12/780,685, dated Aug. 16, 2012 (16 pages).
Third Office Action in U.S. Appl. No. 12/780,685, dated Jan. 2, 2014 (20 pages).
Fourth Office Action in U.S. Appl. No. 12/780,685, dated Jun. 16, 2014 (27 pages).
Fifth Office Action in U.S. Appl. No. 12/780,685, dated Jan. 5, 2015 (25 pages).

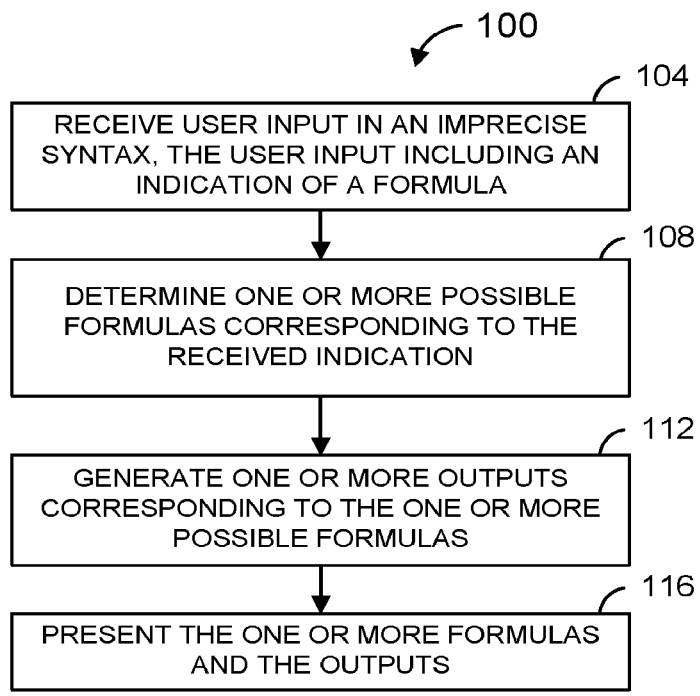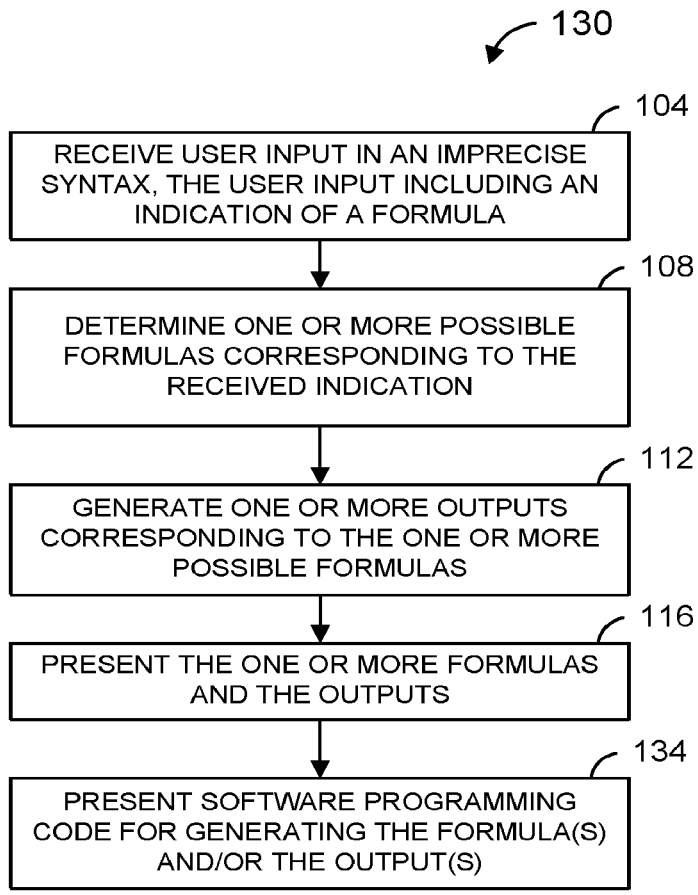

FIG. 3A

ENTER A FORMULA:  ⌐ 154
X SQUARED
GET FORMULA
⌐ 158

FIG. 3B

ENTER A FORMULA:  ⌐ 154
X SQUARED
GET FORMULA
⌐ 158

⌐ 162

| You Entered: | $x^2$ |
|---|---|
| Plot: | [graph of parabola from -1.5 to 1.5, y-axis 0 to 1.2] 204 |
| Real roots: | x = 0 |
| Derivative: | $\frac{d}{dx}(x^2) = 2x$ |
| Indefinite Integral: | $\int x^2 dx = \frac{x^3}{3}$ |
| Global minimum: | min {$x^2$} = 0 at x = 0 |

ENTER A FORMULA: ⟵ 204

RATE REACTION, POTASSIUM PERSULFATE, POTASSIUM IODIDE

GET FORMULA
⟵ 208

⟵ 212

You Entered: RATE OF REACTION OF POTASSIUM PERSULFATE ($K_2S_2O_8$) WITH POTASSIUM IODIDE (KI)
216

Reaction: $S_2O_8^{2-}$ + $2I^-$ ⟶ $2SO_4^{2-}$ + $I_2$
PERSULFATE   IODIDE              SULFATE        IODINE
220

Rate of Reaction:
RATE OF REACTION = $k*(S_2O_8^{2-})^p(I^{1-})^q$

WHERE:

$k = Ae^{-E_a/RT}$
A = ARRHENIUS CONSTANT
$E_a$ = ACTIVATION ENERGY OF REACTION
T = ABSOLUTE TEMPERATURE
R = UNIVERSAL CONSTANT OF GASES
p = ORDER OF THE REACTION WITH RESPECT TO PERSULFATE
q = ORDER OF THE REACTION WITH RESPECT TO IODIDE
224

Natural Log of Rate of Reaction:
ln(RATE OF REACTION) = ln(k) + p ln($S_2O_8^{2-}$) + q ln($I^{1-}$)
228

```
                                          ┌─700
┌────────────────────────────────────────────────────────────────┐
│ Enter numbers, formulas, units, dates, etc...  ┌─704  Examples >> │
│ ┌────────────────────────────────────────────────────────────┐ │
│ │ Int Log x                                                   │ │
│ └────────────────────────────────────────────────────────────┘ │
│ ┌────────────────────────────────────────────────────────────┐ │
│ │ Integrate[Log[x],x]                                         │ │
│ └────────────────────────────────────────────────────────────┘ │
│ ┌─────────┐                                                     │
│ │CALCULATE│                                                     │
│ └─────────┘                                                     │
│      ╲708              ┌─712                                    │
│ ┌────────────────────────────────────────────────────────────┐ │
│ │ Input:                                                      │ │
│ │   ∫log(x)dx                                                 │ │
│ │                                                             │ │
│ │                          log(x) is the natural logarithm >> │ │
│ └────────────────────────────────────────────────────────────┘ │
└────────────────────────────────────────────────────────────────┘
```

FIG. 14

```
                                          ┌─720
┌────────────────────────────────────────────────────────────────┐
│ Enter numbers, formulas, units, dates, etc...  ┌─724  Examples >> │
│ ┌────────────────────────────────────────────────────────────┐ │
│ │ Integral Log x                                              │ │
│ └────────────────────────────────────────────────────────────┘ │
│ ┌────────────────────────────────────────────────────────────┐ │
│ │ Integrate[Log[x],x]                                         │ │
│ └────────────────────────────────────────────────────────────┘ │
│ ┌─────────┐                                                     │
│ │CALCULATE│                                                     │
│ └─────────┘                                                     │
│      ╲728              ┌─732                                    │
│ ┌────────────────────────────────────────────────────────────┐ │
│ │ Input:                                                      │ │
│ │   ∫log(x)dx                                                 │ │
│ │                                                             │ │
│ │                          log(x) is the natural logarithm >> │ │
│ └────────────────────────────────────────────────────────────┘ │
└────────────────────────────────────────────────────────────────┘
```

FIG. 15

```
                                                           ┌─750
┌─────────────────────────────────────────────────────────────┐
│  Enter numbers, formulas, units, dates, etc...  ┌754    Examples >>
│  ┌────────────────────────────────────────────────────────┐
│  │ 1492                                                   │
│  └────────────────────────────────────────────────────────┘
│  ┌─────────┐
│  │CALCULATE│
│  └─────────┘
│        └─758
```

762 — Input:
1492

764 — Number name:
1 thousand and 492

766 — Roman numerals:
MCDXCII

768 — Binary form:
$10111010100_2$

770 — Prime factorization :
$2^2 37 3^1$

772 — Residues modulo small integers :

| $m$ | 2 | 3 | 4 | 5 | 6 | 7 | 8 | 9 |
|---|---|---|---|---|---|---|---|---|
| 1492 mod $m$ | 0 | 1 | 0 | 2 | 4 | 1 | 4 | 7 |

774 — Properties :
1492 has 1 representation as a sum of 2 squares:
$1492 = 14^2 + 36^2$ 1492 has the representation $1492 = 23^6 + 34$.

1492 divides $89^6 - 1$.

776 — Time from today :
The year 1492 was 514 years ago.

FIG. 16

Assuming a list | %20%22Times%22')">Use multiplication instead

Input :
{3, 4, 5}

Interpolating polynomial :
$a_n = n + 2$

Possible continuation :
3, 4, 5, 6, 7, 8

Total of elements :
12

Descriptive statistics :

| | | |
|---|---|---|
| *Location* | mean | 4.000 |
| | harmonic mean | 3.830 |
| | geometric mean | 3.915 |
| | root mean square | 4.082 |
| | median | 4.000 |
| *Dispersion* | standard deviation | 1.000 |
| | mean deviation | 0.6667 |
| | median deviation | 1.000 |
| | quartile deviation | 0.7500 |
| | sample range | 2.500 |
| *Shape* | skewness | 0 |
| | quartile skewness | 0 |
| | kurtosis | 1.500 |

Pie chart:
□ 25.%
▨ 33.3%
▧ 41.7%

Spherical coordinates (radial, polar, azimuthal) :
$r \approx 7.07107$, $\theta \approx 45°$, $\phi \approx 53.1301°$ Exact form >>

Triangle:
3 right triangle

Diophantine relation:
$3^2 + 4^2 = 5^2$

PERFORMING MACHINE ACTIONS IN RESPONSE TO VOICE INPUT

CROSS-REFERENCE TO RELATED APPLICATION

The present application is a continuation of U.S. patent application Ser. No. 14/082,581, now U.S. Pat. No. 8,966,439, entitled "METHOD AND SYSTEM FOR DETERMINING AN ANSWER TO A QUERY," filed Nov. 18, 2013, which is a continuation of U.S. patent application Ser. No. 11/852,044, now U.S. Pat. No. 8,589,869, entitled "METHODS AND SYSTEMS FOR DETERMINING A FORMULA," filed Sep. 7, 2007, which claims the benefit of U.S. Provisional Application No. 60/842,756, entitled "METHODS AND SYSTEMS FOR DETERMINING A FORMULA," filed on Sep. 7, 2006. All of the applications referenced above are hereby incorporated by reference herein in their entireties.

BACKGROUND

The MATHEMATICA® software system available from Wolfram Research, Inc. is a powerful computational tool that can evaluate general symbolic expressions, as well as mathematical and numeric expressions. MATHEMATICA® is an interpreted language, with a notion of "evaluation" of symbolic expressions. Evaluation consists in applying to any symbolic expression all transformation rules that fit that expression.

In the MATHEMATICA® software system, a user can create interactive electronic documents referred to as "notebooks." Various expressions, including numeric and symbolic expressions, can be entered into a notebook via a keyboard, for example, and a user can cause the expression to be evaluated. As a simple example, a user could first set a function $f$ equal to $x^2$ by typing "f=x^2" and then pressing "Enter" while holding down the "Shift" key (i.e., "hitting Shift-Enter"). Then, the user could have the MATHEMATICA® software system evaluate the integral off with respect to x by typing "integral[f,x]" and then hitting Shift-Enter. Of course, the MATHEMATICA® software system permits users to evaluate much more complex expressions and to analyze complex mathematical and scientific problems.

Input to the MATHEMATICA® software system must be in a particular syntax or MATHEMATICA® will not recognize what the user intended. For example, if a user wants to utilize a built-in function of the MATHEMATICA® software system, such as the function "integral", the user must correctly type in the word "integral." Additionally, the expression that is to be integrated must be included within brackets subsequent to the word "integral". For example, to evaluate the integral off with respect to x, the text "integral [f,x]" must be typed. If the correct syntax is not followed exactly, the MATHEMATICA® software system will not recognize what the user had intended. For example, if a built-in function or a user-defined function is misspelled, MATHEMATICA® will not recognize that the user intended to use the function. Similarly, if a bracket, comma, parentheses, etc. is erroneously omitted or misplaced, MATHEMATICA® will not recognize what the user intended.

Various currently available on-line calculators utilize formulas to generate numerical results based on user-provided parameters. As an example, a website may provide a mortgage payment calculator that uses a mathematical formula to calculate a monthly mortgage payment based on various parameters such as a mortgage amount and an interest rate. A user can input values of the parameters by typing numbers into various text boxes on the web page. For example, the user can input a mortgage amount, an interest rate, number of years, etc. Then, the user can select a "Calculate" button on the web page to generate a mortgage payment, which is presented to the user via a different web page.

Search engines, such as Internet search engines, have been in use for some time. Such search engines permit the user to form a search query using combinations of keywords to search through a web page database containing text indices associated with one or more distinct web pages. The search engine looks for matches between the search query and text indices in the web page database, and then returns a number of hits which correspond to URL pointers and text excerpts from the web pages that represent the closest matches.

Some Internet search engines analyze the context of keywords in order to narrow the number of matches. For example, if a search query includes the words "yellow" and "pages," a search engine may recognize that the phrase "yellow pages" has a particular meaning and it may therefore note that web pages including the phrase "yellow pages" may be a closer match than web pages merely containing the word "yellow" and/or the word "pages."

Some application programs, for example, a word processor, may have a help tool that allows a user to enter a word or phrase and will display help topics containing that word or phrase, from which the user can make a selection.

BRIEF DESCRIPTION OF THE DRAWINGS

FIG. 1 is a flow diagram of an example method for providing one or more formulas to a user based on an input that may be in an imprecise syntax;

FIG. 2 is a flow diagram of another example method for providing one or more formulas to a user based on an input that may be in an imprecise syntax;

FIG. 3A is an illustration of an example display that may be utilized in an implementation of the method of FIG. 1;

FIG. 3B is an illustration of the example display of FIG. 3A after the user has activated a button;

FIG. 4 is an illustration of another example display that may be utilized in an implementation of the method of FIG. 1;

FIG. 13 is an illustration of another example display that may be utilized in an implementation of the method of FIG. 1;

FIG. 14 is an illustration of yet another example display that may be utilized in an implementation of the method of FIG. 1;

FIG. 15 is an illustration of still another example display that may be utilized in an implementation of the method of FIG. 1;

FIG. 16 is an illustration of yet another example display that may be utilized in an implementation of the method of FIG. 1;

DETAILED DESCRIPTION

Figure 5:
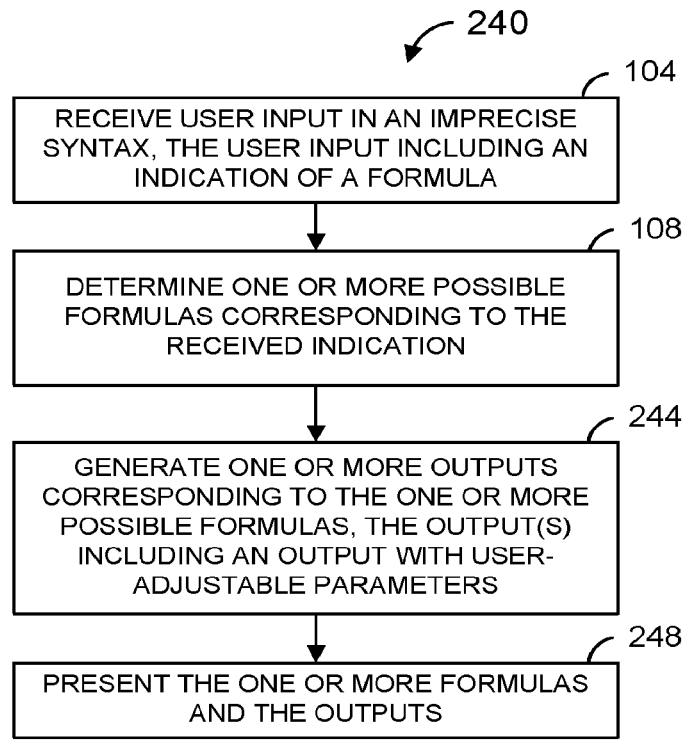
FIG. 5 is a flow diagram of yet another example method for providing one or more formulas to a user based on an input that may be in an imprecise syntax.

Generally speaking, the example methods and systems described herein may help a user to determine a particular formula when the details of the formula are not known to the user. Also, even if the particular formula is known to the user, the example methods and systems may output a formula in a particular syntax in response to the user merely providing a short-hand and/or pseudocode version of the formula. This may be useful if the formula is particularly long or complex and would be time-consuming for the user to write or type, or enter into a document using an equation editor, for example. Thus, a user could enter a relatively small amount of ASCII text, for example, and, in response, a complex equation, formula, etc., including mathematical or scientific symbols could be returned. The ASCII text could include technical shorthand or abbreviations, for example.

A formula, as the term is used herein, may comprise a fact, rule, or principle expressed in scientific, mathematical, or technical symbols, for example. A formula may be a scientific or mathematical formula. An example of a mathematical formula is a mathematical expression defining the area of a triangle based on the lengths of the triangle's sides. A user could enter as an input to a system described herein the text "area of a triangle," and the system may return a formula for determining the area of a triangle based on the lengths of the triangle's sides. Additionally, the system may return a formula for determining the area of a triangle based on the lengths of two sides and the angle between the sides. Also, the system may return a formula for determining the area of a triangle based on the base and height of the triangle. Further, the system may generate and return other information related to the formula(s). For example, it may generate and return a plot of the formula, an integral of the formula, a derivative of the formula, etc. An example of a scientific formula may be a chemical formula.

A formula also may be an expression in a precise syntax, such as a software programming language statement, a database query, etc.

FIG. 1 is a flow diagram of an example method 100 for providing one or more formulas to a user based on an input that may be in an imprecise syntax. An imprecise syntax is in contrast to a typical computer programming language syntax, in which exact spelling, exact placement of punctuation, exact placement of parentheses, etc. is necessary to specify a particular formula. Similarly, with typical computer programming language syntax, a slight change in punctuation, for example, could specify a completely different formula or could render a computer language statement meaningless to a compiler. On the other hand, with an imprecise syntax, a formula can be expressed using language and terms that may be readily understandable to a human, but unintelligible to a computer program such as a compiler. Additionally, with an imprecise syntax, many different variations of language and terms and groupings of language and terms may correspond to one formula. As will be described below, the method 100 may permit a user to obtain precise formulas by inputting names or descriptions of the formulas in text, inputting pseudo code, inputting incorrectly expressed computer language statements, etc.

The method 100 could be implemented, at least partially, by a server system in conjunction with a website, for example. In this context, a user could access the website using a browser running on a personal computer, cell phone, personal digital assistant (PDA), etc., for example, and could utilize the website to obtain formulas and/or outputs related to the formulas. It will be understood, however, that the method 100 could also be used in other contexts. For example, the method 100 could be implemented, at least partially, as part of a "Help" system of a software application such as a computational tool. In such a context, the user could use the "Help" system to obtain formulas and/or outputs related to the formulas.

At a block 104, user input in an imprecise syntax may be received, the input including an indication of a formula. For example, a user may input the text "area of a triangle" into an input field of a web page, a "Help" screen, etc. This entered text may be received, for example, by a web site server system via the Internet, another computer communicatively coupled to the user's computer via a network, an application running on the user's computer, etc. The user input may also include indications of values of parameters to be used in the formula. For example, a user may input the text "area of a triangle length of sides 3, 4, 5".

At a block 108, one or more possible formulas corresponding to the received indication of the formula may be determined. Because the syntax of the received indication is imprecise, there may be multiple formulas that possibly may correspond to the indication. Additionally, there may exist multiple formulas for determining the same desired result. For example, if the received input includes the text "area of a triangle," there are multiple formulas for determining the area of a triangle such as:

$$\text{Area} = \tfrac{1}{2} * \text{base} * \text{height} \qquad (\text{Equ. 1})$$

$$\text{Area} = \tfrac{1}{2} * A * B * \sin(\alpha) \qquad (\text{Equ. 2})$$

where A is the length of a first side, B is the length of a second side, and α is the angle between the first and second sides, and $$\text{Area} = \sqrt{s(s-A)(s-B)(s-C)} \qquad (\text{Equ. 3})$$

where $$s = \frac{A+B+C}{2} \qquad (\text{Equ. 4})$$

Because the syntax of the indicator may be imprecise and/or because there may exist multiple formulas for determining one desired result, it is possible that a relatively large number of possible formulas and/or formulas not likely to be relevant may be determined at the block 108. Thus, optionally, formulas that are less likely to be relevant than others may be omitted or eliminated. For example, a ranking procedure may be utilized to determine which formulas are not likely to be relevant and which formulas should be omitted or eliminated.

For certain inputs of the user, a process or system that implements the block 108 may be unable to determine a formula based on the data received at the block 104. Additionally, it may be determined that the number of possible formulas is high, and additional information may help reduce the number. Thus, in some implementations, the user may be prompted for additional information that may help to determine formula or formulas. For example, if the data received at the block 104 is ambiguous as to the formula or formulas it may indicate, the user may be prompted to provide additional information to help clear up or reduce the ambiguity. For instance the user could be prompted to input additional text, to select one or possibly a plurality of items from a list, to answer one or more yes or no or multiple choice questions, etc. As yet another example, the user could be prompted to talk with a human operator, via telephone, email, instant messaging, for example, to ascertain the formula that the user was trying to indicate. The human operator could then provide additional information to the process or system or configure the process or system to interpret such an input and/or similar inputs in the future. Alternatively, if the process or system that implements the block 108 is unable to determine a formula based on the data received at the block 104, the user may be so notified and the method 100 may terminate.

At a block 112, one or more outputs corresponding to the one or more formulas determined at the block 108 may be generated. For example, if the user input received at the block 104 includes indications of parameters, an output of the formula having the parameters integrated therein may be generated. For example, if the user entered the text "area of a triangle length of sides 3, 4, 5," an output such as an output showing the side lengths inserted in Equations 3 and 4 could be generated. Also, if the user has entered enough parameters to compute a numerical result, such a result may be generated.

Additionally, other types of outputs may be generated, including outputs mathematically or otherwise related to the formula. For example, for each formula, one or more or none of the following may optionally be generated: a derivative of the formula, an integral of the formula, roots of the formula, one or more plots of the formula or an evaluation of the formula, data related to the formula or an evaluation of the formula, etc. If multiple formulas were determined at the 108, such other outputs need not be generated for each formula. For instance, such other outputs could be generated for only the top one, two, three, etc., ranked formulas could be generated.

At a block 116, the formula(s) determined at the block 108 and the output(s) generated at the block 112 may be presented to the user. This may comprise transmitting the information from a web site server system to the user's computer via the Internet, transmitting the information from a computer to the user's computer via a network, etc. If the information is transmitted to the user's computer via the Internet, presenting the information may include displaying a web page to the user. If other blocks of the method 100 are implemented using software executed by the user's computer, presenting the information need not comprise transmitting information via a network. For instance, the blocks 108 and 112 could be implemented on the user's computer, and the formula(s) determined at the block 108 and the output(s) generated at the block 112 could be displayed in a window without having to first transmit the formula(s) and the output(s) to the user's computer.

Although graphical user interface mechanisms were described above, mechanical user interfaces may be utilized as well such as game controllers, joysticks, knobs, dials, etc. Similarly, although rendering a numerical result on a display device was described above, other types of rendering may be implemented such as sending the numerical result to a file or to another software application, or using the numerical result to generate audio, control light emitting diodes, control a stepper motor, etc.

FIG. 2 is a flow diagram of another example method 130 for providing one or more formulas to a user based on an input that may be in an imprecise syntax. The method 130 includes the same blocks 104, 108, 112, and 116 as in the method 100 of FIG. 1. Similar to the method 100 of FIG. 1, in some implementations, the user also may be prompted for additional information that may help to determine formula or formulas. Additionally, the method 130 includes a block 134, at which software programming code for generating one or more of the formula(s) (block 108) and/or one or more of the output(s) (block 112) is presented to the user. The software programming code could be presented in a web page or a window, for example. The software programming code could be presented in the same web page or window used to present the formula(s) and the output(s) at the block 116.

The software programming code could comprise commands in any of a variety of computer programming languages. For example, the software programming code could comprise code that is to be compiled, such as C programming language code, C++ programming language code, C# programming language code, etc. Also, the software programming code could comprise code that is to be interpreted. Additionally, the software programming code could comprise code to be used in a computational tool such as a spreadsheet application, the MATHEMATICA® software system available from Wolfram Research, Inc., etc. Other types of software programming code could include Java programming language code, Visual Basic programming language code, etc.

In one implementation, presenting the software programming code may comprise providing a mechanism for inserting the code in a file. For instance, the web page, window, etc., in which the code is presented could include a button or some other mechanism by which the code could be inserted in a source code file, a notebook, a spreadsheet, etc. For example, when the mechanism is activated, the code could be inserted at the end of a file, at a position of a cursor, at a position of a selected spreadsheet cell or cells, etc.

FIG. 3A is an illustration of an example display 150 that may be utilized in an implementation of the method 100 of FIG. 1. The example display 150 is configured to permit a user to enter an input that includes an indication of a formula. As describe previously, the input may be in an imprecise syntax. The display 150 may be part of a web page, window, etc., for example.

The display 150 includes a field 154 in which a user may type text. In the illustration of FIG. 3A, a user has typed the text "X SQUARED" into the field 154. The display 150 also includes a button 158 that a user may activate to initiate a determination of the formula corresponding to the text in the field 154. In the illustration of FIG. 3A, the formula corresponding to the text is simply the symbolic expression $x^2$.

FIG. 3B is an illustration of the example display 150 after the user has activated the button 158. In particular, the display 150 is now modified to include a portion 162 which includes several fields 166, 170, 174, 178, 182, and 186. The field 166 displays the formula (i.e., the symbolic expression $x^2$) determined based on the text entered into the field 154.

The portion 162 of the display 150 also includes other outputs that are mathematically related to the formula. For example, the field 170 includes a plot of $x^2$. The field 174 includes the real roots of $x^2$. The field 178 includes the derivative of $x^2$, and the field 182 includes the indefinite integral of $x^2$. Also, the field includes the global minimum of $x^2$.

FIG. 4 is an illustration of another example display 200 that may be utilized in an implementation of the method 100 of FIG. 1. Similar to the display 150 of FIGS. 3A and 3B, the display 200 includes an input field 204 and a button 208. In the illustration of FIG. 4, a user has entered the text "RATE REACTION, POTASSIUM PERSULFATE, POTASSIUM IODIDE" into the field 204. Also, the display 200 includes a portion 212 that was generated in response to the user entering the text in the field 204 and activating the button 208.

The portion 212 includes several fields 216, 220, 224, and 228. The field 216 includes an indication of the formula that was determined based on the text provided by the user in the field 204. The field 220 displays a chemical reaction formula that is related to the formula determined based on the text in the field 204. In particular, the field 220 displays the chemical reaction formula of persulfate ($S_2O_8^{2-}$) reacting with iodide ($2I^-$) to produce sulfate ($SO_4^{2-}$) and iodine ($I_2$). The field 224 displays the rate of reaction formula, and the field 228 displays a different mathematical form of the rate of reaction formula.

Referring again to FIGS. 1 and 2, the formulas to be determined may be from a variety of fields such as mathematics, chemistry, physics, finance, engineering, medicine, etc. In some implementations, a single system that implements a method such as the method 100, the method 130, or some other method, may be configured to determine formulas from a plurality of fields. In other implementations, a system may be configured to determine formulas from only one field. For example, a system may be configured to determine finance-related formulas, whereas a different system may be configured to determine physics-related formulas.

FIG. 5 is a flow diagram of yet another example method 240 for providing one or more formulas to a user based on an input that may be in an imprecise syntax. The method 240 includes the same blocks 104 and 108 as in the methods 100 and 130 of FIGS. 1 and 2. Similar to the method 100 of FIG. 1, in some implementations, the user also may be prompted for additional information that may help to determine formula or formulas.

Figure 6:
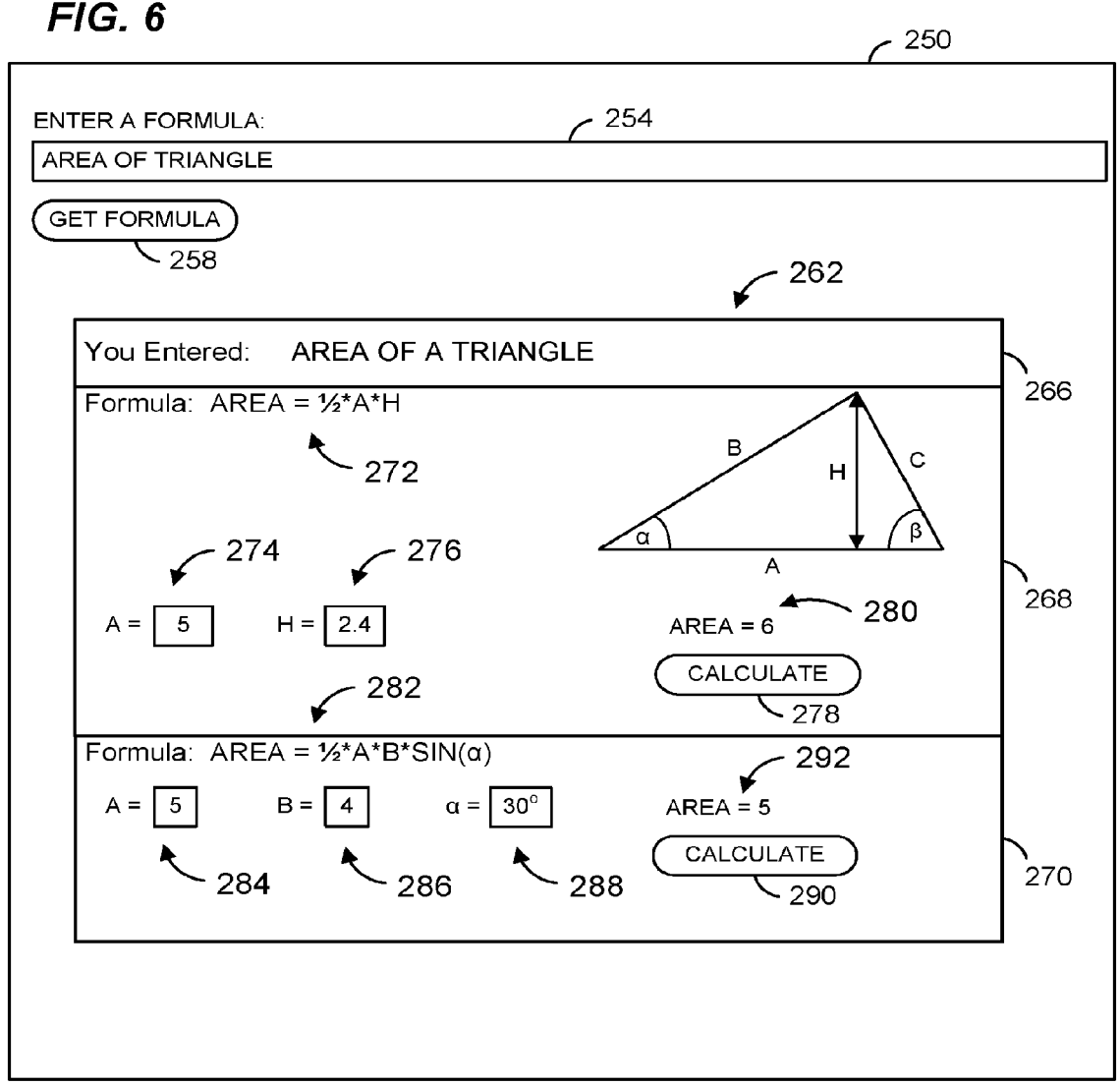
FIG. 6 is an illustration of an example display that may be utilized in an implementation of the method of FIG. 5.

Additionally, the method 240 includes a block 244, at which one or more outputs corresponding to the one or more formulas determined at the block 108 may be generated, the one or more output including one or more outputs having user-adjustable parameters. Referring now to FIG. 6, an illustration of an example display 250 that may be utilized in an implementation of the method 240 of FIG. 5 is provided. Similar to the display 150 of FIGS. 3A and 3B, and the display 200 of FIG. 4, the display 250 includes an input field 254 and a button 258. In the illustration of FIG. 6, a user has entered the text "AREA OF A TRIANGLE" into the field 254. Also, the display 250 includes a portion 262 that was generated in response to the user entering the text in the field 254 and activating the button 258.

The portion 262 includes several fields 266, 268, and 270. The field 266 includes an indication of the formula(s) that was determined based on the text provided by the user in the field 254. The field 268 includes an indication 272 of a first formula for determining the area of a triangle based on a base length (A) and a height (H). In particular, the field 268 displays the formula AREA=½*A*H. The field 268 also includes a plurality of user interface mechanisms for permitting the user to adjust parameters of the formula 272. For example, the field 268 includes a text box 274 in which a user can enter a value of A, a text box 276 in which a user can enter a value of H, and a button 278 by which the user can cause a numerical value of the AREA to be calculated. After activating the button 278, a value of the AREA may be displayed in a portion 280. Although the example display 250 includes text boxes for entering parameter values, other user interface mechanisms may be used such as sliders, knobs, pull-down menus, buttons, etc. Similarly, although the example display 250 includes a button 278 for causing a result to be calculated, other techniques may be utilized. For example, the result could be calculated in response to text being entered in a text box or a slider being moved, for example. The user adjustable parameter and result calculation functionality of the display 250 may be implemented using a variety of techniques. For example, if the display 150 is part of a web page, applets or some other suitable technique may be utilized such as client-side or server-side controls (e.g., Active Server Page (ASP) technology available from Microsoft®, common gateway interface (CGI) technology, Fast CGI, Java Server Page technology, hyper text markup language (HTML) controls, ActiveX controls, Web Form controls available from Microsoft®, java controls, etc.). Additionally, techniques such as described in U.S. patent application Ser. No. 11/234,550, filed Sep. 23, 2005, entitled "Method of Dynamically Linking Objects Operated on by a Computational System," which is hereby incorporated by reference, may optionally be utilized to implement the user adjustable parameter functionality of the display 250.

The field 270 includes an indication 282 of a second formula for determining the area of a triangle based on a first side length (A), a second side length (B), and an angle ($\alpha$) between the first and second sides. In particular, the field 270 displays the formula AREA=½*A*B*SIN($\alpha$). The field 270 also includes a plurality of user interface mechanisms for permitting the user to adjust parameters of the formula 282. For example, the field 270 includes a text box 284 in which a user can enter a value of A, a text box 286 in which a user can enter a value of b, a text box 288 in which a user can enter a value of $\alpha$, and a button 290 by which the user can cause a numerical value of the AREA to be calculated. After activating the button 290, a value of the AREA may be displayed in a portion 292.

Referring again to FIG. 5, the block 244 may also comprise generating outputs similar to those described above with respect to the block 112 of FIG. 1.

At a block 248, the formula(s) determined at the block 108 and the output(s) generated at the block 244 may be presented to the user. This may comprise transmitting the information from a web site server system to the user's computer via the Internet, transmitting the information from a computer to the user's computer via a network, etc. If the information is transmitted to the user's computer via the Internet, presenting the information may include displaying a web page to the user. If other blocks of the method 240 are implemented using software executed by the user's computer, presenting the information need not comprise transmitting information via a network. For instance, the blocks 108 and 244 could be implemented on the user's computer, and the formula(s) determined at the block 108 and the output(s) generated at the block 244 could be displayed in a window without having to first transmit the formula(s) and the output(s) to the user's computer.

Optionally, the method 240 may also comprise presenting to the user software programming code for generating one or more of the formula(s) (block 108) and/or one or more of the output(s) (block 244). The software programming code could be presented in a web page or a window, for example. The software programming code could be presented in the same web page or window used to present the formula(s) and the output(s) at the block 248. The software programming code could comprise commands in any of a variety of computer programming languages, such as the programming languages described above with reference to FIG. 2.

In one implementation, presenting the software programming code may comprise providing a mechanism for inserting the code in a file. For instance, the web page, window, etc., in which the code is presented could include a button or some other mechanism by which the code could be inserted in a source code file, a notebook, a spreadsheet, etc. For example, when the mechanism is activated, the code could be inserted at the end of a file, at a position of a cursor, at a position of a selected spreadsheet cell or cells, etc.

Figure 7:
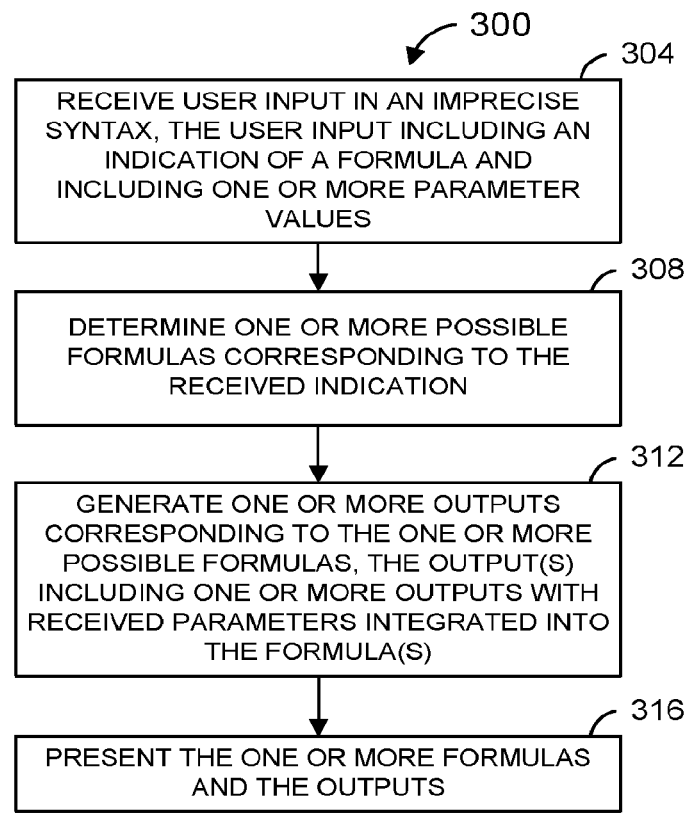
FIG. 7 is a flow diagram of still another example method for providing one or more formulas to a user based on an input that may be in an imprecise syntax.

FIG. 7 is a flow diagram of still another example method 300 for providing one or more formulas to a user based on an input that may be in an imprecise syntax. At a block 304, user input in an imprecise syntax may be received, the input including an indication of a formula and also including indication(s) of one or more parameter values related to the formula. The method may include a block 308, similar to the block 108 of FIG. 1, at which one or more formulas corresponding to the indication of the formula received at the block 304 are determined. Similar to the method 100 of FIG. 1, in some implementations, the user also may be prompted for additional information that may help to determine formula or formulas.

Figure 8:
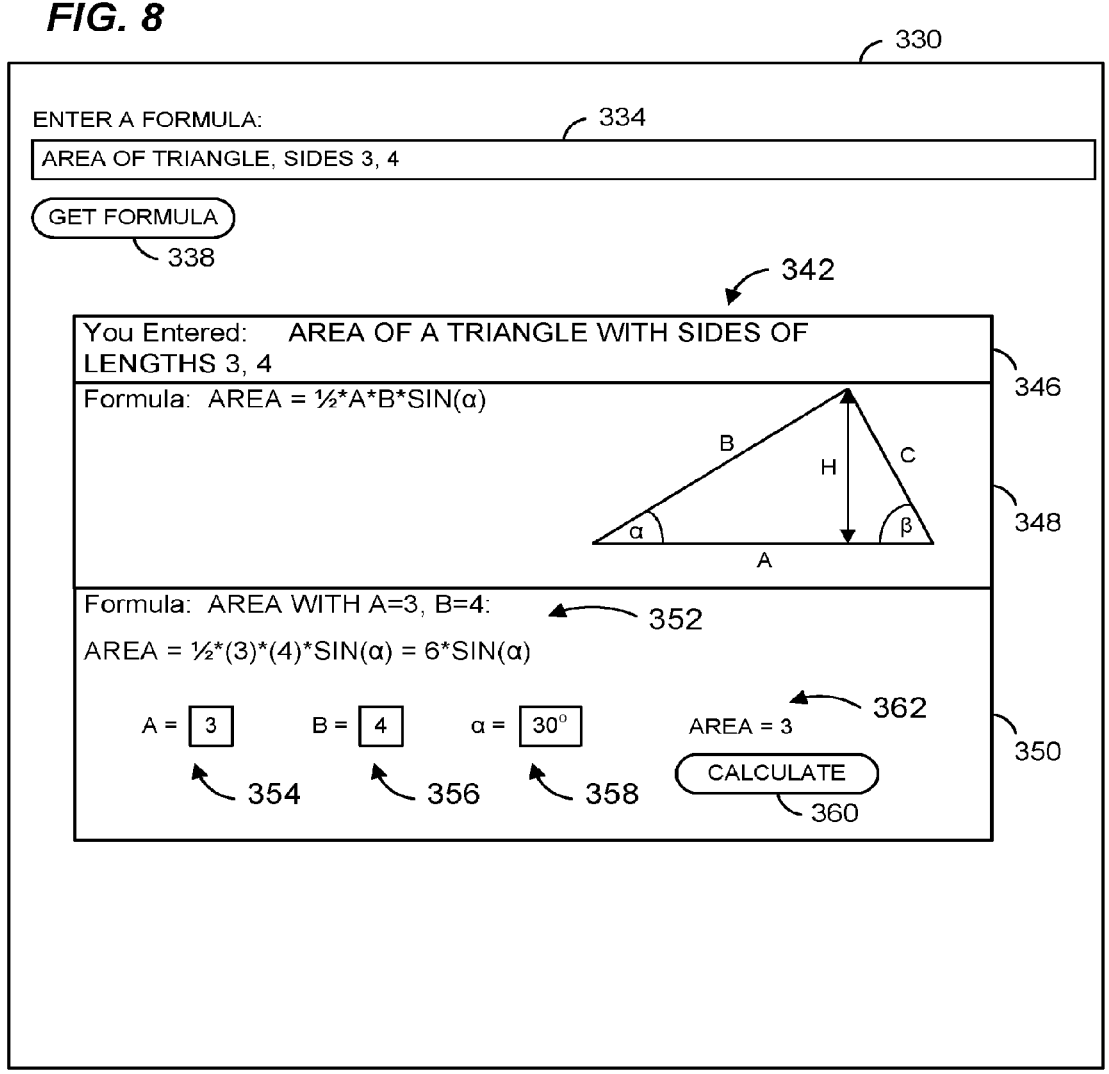
FIG. 8 is an illustration of an example display that may be utilized in an implementation of the method of FIG. 7.

Additionally, the method 300 includes a block 312, at which one or more outputs corresponding to the one or more formulas determined at the block 308 may be generated. The output(s) may include one or more outputs in which parameter values corresponding to the parameter value indications received at the block 304 are integrated with at least some of the one or more formulas determined at the block 308. Referring now to FIG. 8, an illustration of an example display 330 that may be utilized in an implementation of the method 300 of FIG. 7 is provided. Similar to the display 150 of FIGS. 3A and 3B, and the display 200 of FIG. 4, the display 330 includes an input field 334 and a button 338. In the illustration of FIG. 8, a user has entered the text "AREA OF A TRIANGLE, SIDES 3, 4" into the field 334. Also, the display 330 includes a portion 342 that was generated in response to the user entering the text in the field 334 and activating the button 338.

The portion 342 includes several fields 346, 348, and 350. The field 346 includes an indication of the formula(s) that was determined based on the text provided by the user in the field 334. The field 348 includes an indication 352 of the formula for determining the area of a triangle with the parameter values indicated in the field 334 having been integrated into the formula.

Referring again to FIG. 7, the block 312 may also comprise generating outputs similar to those described above with respect to the block 112 of FIG. 1. Similarly, the block 312 may also comprise generating outputs similar to those described above with respect to the block 244 of FIG. 5. For instance, referring again to FIG. 8, the field 350 also includes a plurality of user interface mechanisms for permitting the user to adjust parameters of the formula. For example, the field 352 includes a text box 354 in which a user can enter a value of A, a text box 356 in which a user can enter a value of B, a field 358 in which a user can enter a value of a, and a button 360 by which the user can cause a numerical value of the AREA to be calculated. After activating the button 360, a value of the AREA may be displayed in a portion 362. Although the example display 330 includes text boxes for entering parameter values, other user interface mechanisms may be used such as sliders, knobs, pull-down menus, buttons, etc. Similarly, although the example display 330 includes a button 360 for causing a result to be calculated, other techniques may be utilized. For example, the result could be calculated in response to text being entered in a text box or a slider being moved, for example. The user adjustable parameter and result calculation functionality of the display 330 may be implemented using a variety of techniques such as those described above with respect to FIG. 6. In other implementations, the display 330 may permit a user to adjust fewer numbers of parameters as compared to the illustration in FIG. 8. For example, a user could be permitted to adjust the angle α, but not the sides A and B.

Referring again to FIG. 7, at a block 316, the formula(s) determined at the block 308 and the output(s) generated at the block 312 may be presented to the user. This may comprise transmitting the information from a web site server system to the user's computer via the Internet, transmitting the information from a computer to the user's computer via a network, etc. If the information is transmitted to the user's computer via the Internet, presenting the information may include displaying a web page to the user. If other blocks of the method 300 are implemented using software executed by the user's computer, presenting the information need not comprise transmitting information via a network. For instance, the blocks 308 and 312 could be implemented on the user's computer, and the formula(s) determined at the block 308 and the output(s) generated at the block 312 could be displayed in a window without having to first transmit the formula(s) and the output(s) to the user's computer.

Optionally, the method 300 may also comprise presenting to the user software programming code for generating one or more of the formula(s) (block 308) and/or one or more of the output(s) (block 312). The software programming code could be presented in a web page or a window, for example. The software programming code could be presented in the same web page or window used to present the formula(s) and the output(s) at the block 316. The software programming code could comprise commands in any of a variety of computer programming languages, such as the programming languages described above with reference to FIG. 2.

In one implementation, presenting the software programming code may comprise providing a mechanism for inserting the code in a file. For instance, the web page, window, etc., in which the code is presented could include a button or some other mechanism by which the code could be inserted in a source code file, a notebook, a spreadsheet, etc. For example, when the mechanism is activated, the code could be inserted at the end of a file, at a position of a cursor, at a position of a selected spreadsheet cell or cells, etc.

Figure 9:
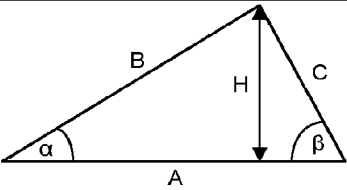
FIG. 9 is an illustration of another example display that may be utilized in an implementation of the method of FIG. 7.

FIG. 9 is an illustration of another example display 370 that may be utilized in an implementation of the method 300 of FIG. 7. Similar to the display 150 of FIGS. 3A and 3B, and the display 200 of FIG. 4, the display 370 includes an input field 374 and a button 378. In the illustration of FIG. 9, a user has entered the text "AREA OF A TRIANGLE, SIDES 3, 4, 5" into the field 374. Also, the display 330 includes a portion 382 that was generated in response to the user entering the text in the field 374 and activating the button 378. The portion 382 includes an indication of a formula for determining the area of a triangle with the parameter values indicated in the field 374 having been integrated into the formula.

Figure 10:
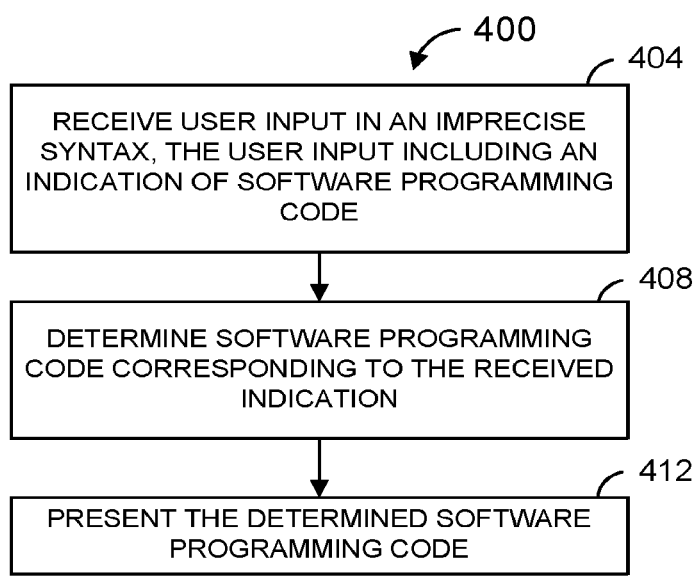
FIG. 10 is a flow diagram of yet another example method for providing one or more formulas to a user based on an input that may be in an imprecise syntax.

FIG. 10 is a flow diagram of yet another example method 400 for providing one or more formulas to a user based on an input that may be in an imprecise syntax. The method 400 may be used to assist a programmer in developing software programming code, for example. At a block 404, user input may be received, the input including an indication of software programming code. The indication may include one or more of pseudo code, software programming code having an incorrect syntax, or software programming code having a correct syntax, etc. In some implementations, the indication may include two or more of pseudo code, software programming code in an incorrect syntax, or software programming code in a correct syntax. For example, the user input could be a mixture of pseudocode and software programming code in one or more languages. Additionally, the software programming code could include code in a mixture of correct and incorrect syntax.

At a block 408, software programming code having a precise syntax corresponding to the indication received at the block 404 may be determined. This may comprise, for example, determining software programming code having a precise syntax corresponding to pseudo code entered in the block 404, determining software programming code having a precise syntax corresponding to software programming code having an incorrect syntax entered in the block 404, determining different software programming code in a precise syntax corresponding to software programming code having the correct syntax entered in the block 404 (e.g., more efficient software programming code, code in a different software programming language, etc.), etc. Similar to the method 100 of FIG. 1, in some implementations, the user also may be prompted for additional information that may help to determine the software programming code.

The block 408 may include determining multiple sets of software programming code having precise syntax. For example, there might be multiple interpretations of the input received at the block 404, and the multiple sets of software programming code may be in the same programming language and may correspond to the multiple interpretations. For instance, different sets of code may correspond to different algorithms, the same algorithm with different initial conditions or other parameters, etc. As another example, the multiple sets of software programming code may correspond to different implementations in the same programming language of essentially the same algorithm. As yet another example, the multiple sets of software programming code may correspond to different implementations in different programming languages.

If multiple sets of software programming code are determined at the block 408, the block 408 optionally may include evaluating the multiple sets to eliminate sets and/or rank sets. For example, sets may be evaluated for code size, memory use efficiency, etc. Also, code sets that result in unwanted operations such as a "divide-by-zero", an infinite loop, etc., may be eliminated.

At a block 412, the software programming code (or multiple sets) determined at the block 408 may be presented to the user. The software programming code could be presented in a web page or a window, for example. The software programming code could be presented in the same web page or window used to present the formula(s) and the output(s) at the block 316. The software programming code could comprise commands in any of a variety of computer programming languages, such as the programming languages described above with reference to FIG. 2.

In one implementation, presenting the software programming code may comprise providing a mechanism for inserting the code in a file. For instance, the web page, window, etc., in which the code is presented could include a button or some other mechanism by which the code could be inserted in a source code file, a notebook, a spreadsheet, etc. For example, when the mechanism is activated, the code could be inserted at the end of a file, at a position of a cursor, at a position of a selected spreadsheet cell or cells, etc.

In one implementation, the example method 400 could be used to assist a user in developing code in a particular software programming language. For example, the method 400 could allow a user to enter code in a first software programming language or in a mixture of first software programming languages, and receive code in a second software programming language to implement what is generally specified by the code entered by the user.

With regard to the example methods of FIGS. 1, 2, 5, 7 and 10, it will be understood by those of ordinary skill in the art that if implemented in a web-based or distributed system, they may be implemented with multiple server systems. For example, a first server system may provide web pages to allow a user to input data indicative of a formula. The first server system may then transmit the input to a second server system that may determine a formula, software programming code, related outputs, etc., as described above. The second server system may then transmit display data and/or other outputs it generates back to the first server system, and the first server system may in turn transmit the display data/outputs to the user computer. Such an implementation may be appropriate for enhancing the capabilities of a standard web-based search engine implemented by the first server system, for example.

Also, in some implementations, presentation of the formula may be omitted. For example, only evaluations of the formula and/or related outputs may be presented to the user. In some of these implementations, the user input optionally could be required to be input in a precise syntax. Multiple outputs corresponding to the formula could be determined and presented including outputs such as one or more evaluations of the formula, one or more outputs that are mathematically or otherwise related to the formula, etc.

Figure 11:
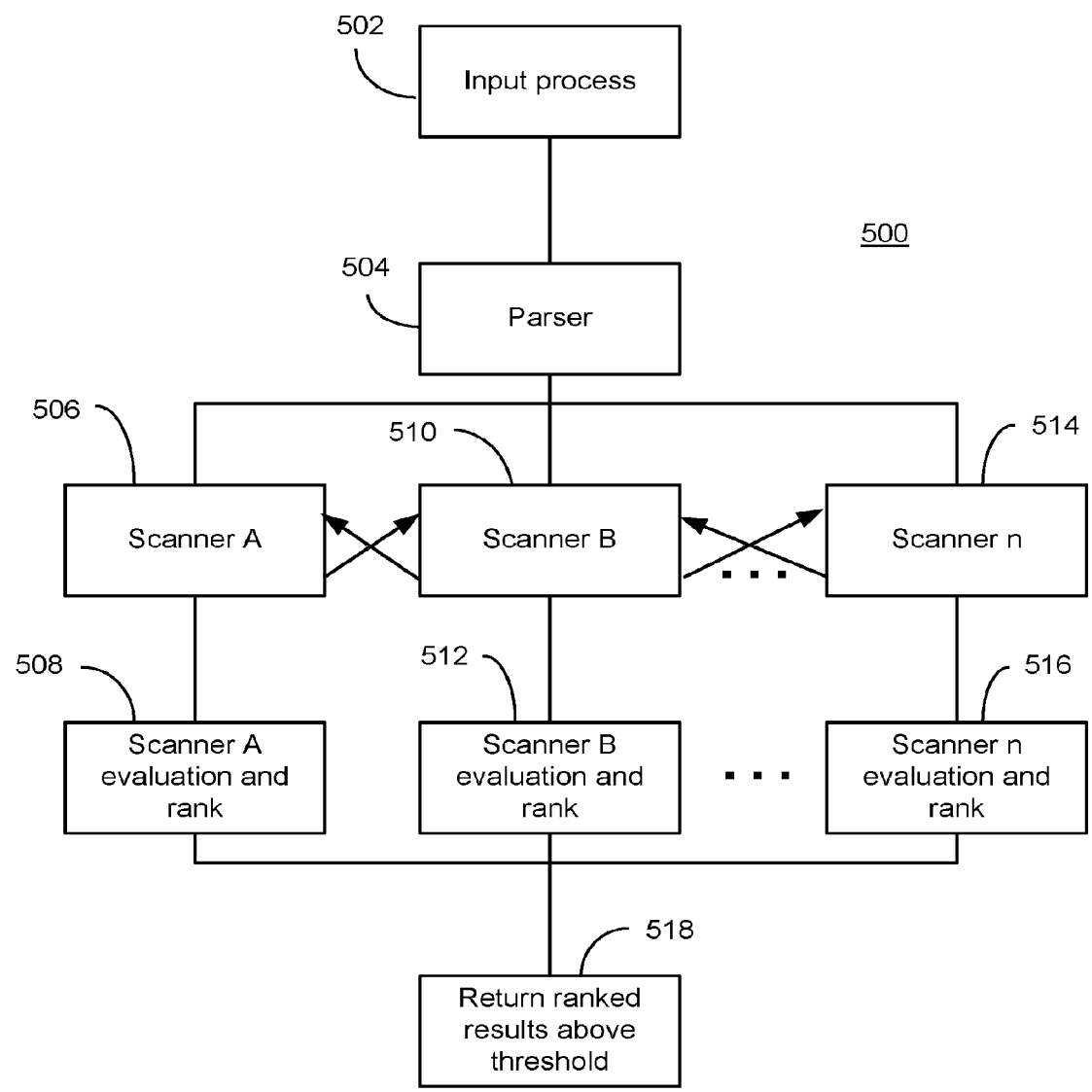
FIG. 11 is a block diagram of an example system for providing one or more formulas to a user based on an input that may be in an imprecise syntax.

FIG. 11 is a block diagram of an example system 500 that may be used to implement one or more of the example methods described previously. Of course other systems may also be used to implement those methods. The system 500 may include an input process 502 for receiving data from a user. The system 500 may be a stand-alone executable application with its own user interface. Also, the system 500 could be an added feature or subsystem of a larger application such as a computational application (e.g., the MATHEMATICA® software system available from Wolfram Research, Inc., a spreadsheet application, etc.). For example, the system 500 could be part of a "help" subsystem within a larger application. Additionally, the system 500 could be an applet accessed via a website, for example. Further, the system 500 may also be implemented as a Web service with a Web browser implementing the user interface in a known manner. For example, the system 500 could be browser plug-in or toolbar system. The input process 502 may receive input in an imprecise syntax. The input process 502 may also provide elementary error and consistency checking, for example, to help ensure that at least some characters are present or prompting the user with an error when a length limit is exceeded.

The system 500 may also include a parser 504 communicatively coupled to the input process 502. The parser 504 may examine the input to extract keywords, group words into phrases, identify numerical expressions, categorize data, etc., for example. The parser 504 may perform an initial go/no go analysis on the keywords, phrases, or numerical expressions to determine if there is enough information to proceed to a further step. When there is not enough information to make even a cursory pass at further analysis, the parser 504 may cause the user to be prompted for additional information such as information that may clarify the formula desired by the user. Alternatively, the system 500 may return the input unchanged along with a message that it cannot interpret the input.

In one implementation, the parser 504 may take an initial input and create tokens, and then assemble the tokens into one or more expressions in a precise syntax. In other words, the parser 504 may generally take input data in an imprecise syntax and generate expressions in a precise syntax. As an example, if a user enters the text "sin[x]<0.5", the parser 504 may create a plurality of tokens: "sin", "[x]", "<", and "0.5", where "sin" is recognized as a function name, "[x]" is recognized as a variable name, "<" is recognized as an inequality, and "0.5" is recognized as a real number. Then, the parser 504 may generate an expression in a precise syntax using these tokens.

Optionally, the parser 504 may perform additional processing. For example, the parser may attempt to identify phrases. Additionally, the parser 504 may attempt to rearrange tokens to see if the rearrangements match something that the parser 504 understands, such as a phrase. For instance, the parser 504 may utilize algorithmic rearrangements of the input. Also, the parser 504 may cause the user to be prompted to rephrase the input. Then, the parser 504 may analyze the original input in conjunction with the rephrased input. Further, the parser 504 may utilize machine learning techniques to identify language processing algorithms that work better than others.

The one or more expressions generated by the parser 504 may be provided to one or more scanners 506, 510, and 514 that may each have a particular focus. For example, scanner A 506 may be directed to developing a graphical plot for numerical expressions or phrases parsed from the input that can be reduced to a plot. As an example, if an input includes an expression, such as $x^2$, scanner A 506 may develop and output a plot of $x^2$ (i.e., a parabola). As another example, if the expression is Sin[x]<0.5, scanner A 506 may develop and output a plot of values of x that satisfy this expression. Other scanners may have other specific specializations, such as evaluating equations, determining roots, evaluating integrals, evaluating derivatives, determining relevant transforms, etc. Other specializations may include, for example, determining mathematical formulas, determining chemical formulas, determining physics formulas, determining financial formulas, determining engineering formulas, determining medical formulas, etc.

Still another specialization may include determining appropriate software programming language code (e.g., generating software programming language code). For instance, a scanner could receive data indicating a mathematical expression and generate software programming language code for evaluating the expression. As an example, a keyword or an expression related to ballistics may cause the scanner to generate software programming code for modeling the height of a projectile and code for modeling the distance of a projectile. In another example, input related to airflow over a wing may return code for modeling turbulent fluid flow over a surface or code for modeling lift and drag in a wing, or both.

Depending upon the application, more or less scanners may be utilized. For instance, if an application is to be devoted for use in a financial field, scanners related to chemical formulas may be omitted.

Some scanners may generate results based on a database query. For example, a scanner related to geometry formulas may query a database for keywords "area" and "triangle" for formulas related to those terms. As another example, a scanner may query a database for raw data needed to evaluate an expression. For instance, an expression may include c, the speed of light, and a scanner may query a database to retrieve a numerical value for c. As another example, an expression may require statistical data, such as a population of a particular city, state, or country needed to evaluate a "per capita" expression, and the scanner may query a statistical database to obtain the needed data.

Other scanners may generate results by synthesizing outputs. For example, a scanner for generating indefinite integrals may receive a mathematical expression and synthesize the indefinite integral of that expression, rather than searching a database of pre-generated indefinite integrals. Some scanners may be capable of doing database queries as well as synthesis of results. For example, the scanner related to geometry formulas may generate an expression for the area of a triangle based on a database query, but may also synthesize another expression by integrating parameter values into formulas retrieved from a database.

In addition to receiving data from the parser 504, each scanner may share results with each of the other scanners. Again, results generated by a scanner based on the shared results may also be shared with each of the other scanners, and so on. This process may continue until the scanners no longer have additional data to add, for example. Trivial transforms may also be recognized and blocked. When each scanner has contributed to both the original input from the parser 504 and shared input from all the other scanners, the results from each scanner to respective postprocessors 508, 512, and 516. The postprocessors 508, 512, 516 evaluate the results and may provide a ranking of each result by assigning a value (e.g., a percentage) to each result.

The ranked results may be passed to an output module 518 which may generate an output having the results with rankings above a certain threshold, while omitting results below the threshold. The threshold may be set at a predetermined level, or may be adjusted according to the number of results and a statistical analysis of the rankings. For example, a query that produces ten thousand results may adjust the threshold to a 99% relevance, thereby limiting the displayed results to the top 100. In another example though, where perhaps only a half a dozen results are returned, all the results may be displayed even though the rankings may be relatively low. The output of the output module 518 may comprise a web page, a window, etc., having one or more formulas. Examples of web pages, windows, etc., that the output module 518 may generate are shown in FIGS. 3A, 3B, 4, 6, 8, 9. When the results include software programming code, the output module 518 may provide a linking function to insert the software programming code into a file such as a notebook in the MATHEMATICA® software system, a source code file, a spreadsheet, etc.

Particularly in a Web Services or comparable environment, scanners may be added or reconfigured based on user needs. For instance, feedback from users or an analysis of user queries may be utilized to add a scanner devoted to a new field (e.g., organic chemistry) or to add further formula data to an existing scanner. Similarly, scanners may be omitted or removed.

Figure 12:
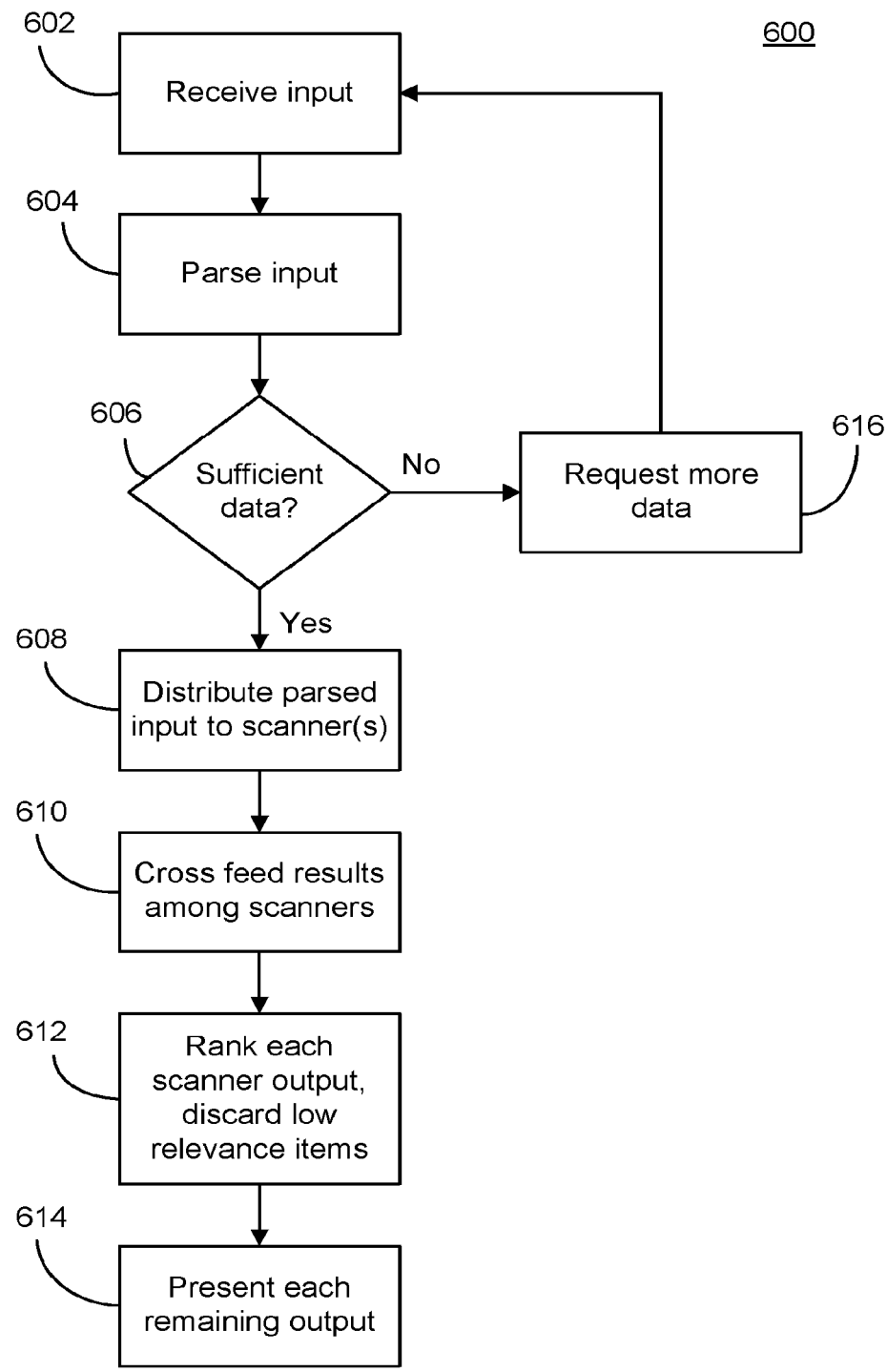
FIG. 12 is a flow diagram of another example method for providing one or more formulas to a user based on an input that may be in an imprecise syntax.

FIG. 12 is flow diagram of yet another example method 600 for providing one or more formulas to a user based on an input that may be in an imprecise syntax. The method 600 will be described with reference to FIG. 11 for ease of explanation. It will be understood, however, that the method 600 may be utilized with systems other than the system 500, and that the system 500 may implement methods other than the method 600.

Input in an imprecise syntax may be received at block 602 and then parsed at block 604 to process the input. For example, the input may be analyzed to create data in a formal or precise syntax. When the parser 504 is able to determine a sufficient amount of data to proceed, a 'yes' branch from a block 606 maybe taken to a block 608. At the block 608, the parsed data (e.g., the output of the parser 504) may be distributed to each of the plurality of scanners 506, 510, 514. As described above, each scanner may examine the output of the parser 504 at the block 608 for areas of specific capability with respect to that scanner. When a scanner identifies data it can process, the scanner creates output specific to the input and then, at a block 610, the scanner may share its output with each of the other scanners. For example, the scanner 506 may create a mathematical expression and that mathematical expression may be delivered to scanners 510 and 514. Scanners 510 and 514 may be able to synthesize output based on the mathematical expression from scanner 506 that they were not able to process from the direct input from the parser 504. When each scanner can no longer synthesize meaningful output, the results may be passed to the output module 518 at a block 612. At the block 512, each output may be ranked in terms of relevance. Output elements of low relevance optionally may be discarded. At a block 614, output elements that were not discarded at the block 612 may be presented to the user. Output elements may be presented in rank order, or in the case of more common output elements, in a standard presentation format.

When the parser 504 cannot process the input, the 'no' branch from the block 606 may be taken to block 616 and the user may be prompted for more information. Alternatively, the user may be prompted that the input cannot be interpreted and the flow may return to the block 602 to receive a next input.

FIG. 13 is an illustration of another example display 700 that may be utilized in an implementation of a method such as the method 100 of FIG. 1. The example display 700 is configured to permit a user to enter an input that includes an indication of a formula. As describe previously, the input may be in an imprecise syntax. The display 700 may be part of a web page, window, etc., for example.

The display 700 includes a field 704 in which a user may type text. In the illustration of FIG. 13, a user has typed the text "int log x" into the field 704. The display 700 also includes a button 708 that a user may activate to initiate a determination of the formula corresponding to the text in the field 704. In the illustration of FIG. 13, a formula corresponding to the text is the symbolic expression ∫log(x)∂x. Thus, if the user activated button 708, the display 700 may display the determined formula in a portion 712.

FIG. 14 is an illustration of another example display 720 that may be utilized in an implementation of a method such as the method 100 of FIG. 1. The display 720 includes a field 724 in which a user may type text. In the illustration of FIG. 14, a user has typed the text "integral log x" into the field 724. The display 720 also includes a button 728 that a user may activate to initiate a determination of the formula corresponding to the text in the field 724. In the illustration of FIG. 14, a formula corresponding to the text is the symbolic expression ∫log(x)∂x. Thus, if the user activated button 728, the display 720 may display the determined formula in a portion 732.

FIG. 15 is an illustration of another example display 750 that may be utilized in an implementation of a method such as the method 100 of FIG. 1. The display 750 includes a field 754 in which a user may type text. In the illustration of FIG. 14, a user has typed the text "1492" into the field 754. The display 750 also includes a button 758 that a user may activate to initiate a determination of the formula corresponding to the text in the field 754. In the illustration of FIG. 15, a formula corresponding to the text is the number 1492. Thus, if the user activated button 758, the display 750 may display information related to the number 1492. For example, the display 750 may include various fields such as the field 762 which indicates the formula (e.g., the number 1492). Other fields 764, 766, 768, 770, 772, 774, and 776 provide information related to the number 1492.

FIG. 16 is an illustration of a portion of another example display 800 that may be utilized in an implementation of a method such as the method 100 of FIG. 1. The portion of the display 800 may be displayed in response to a user entering the text "3 4 5" and activating a button on the display 800. The determined formula is the sequences of numbers {3, 4, 5} and is displayed in a portion 802. The display 800 may display information related to the sequences of numbers {3, 4, 5}. For example, the display 800 may include various fields 804, 806, 808, 810, 812, 814, and 816 that provide information related to the sequences of numbers {3, 4, 5}.

Figure 17:
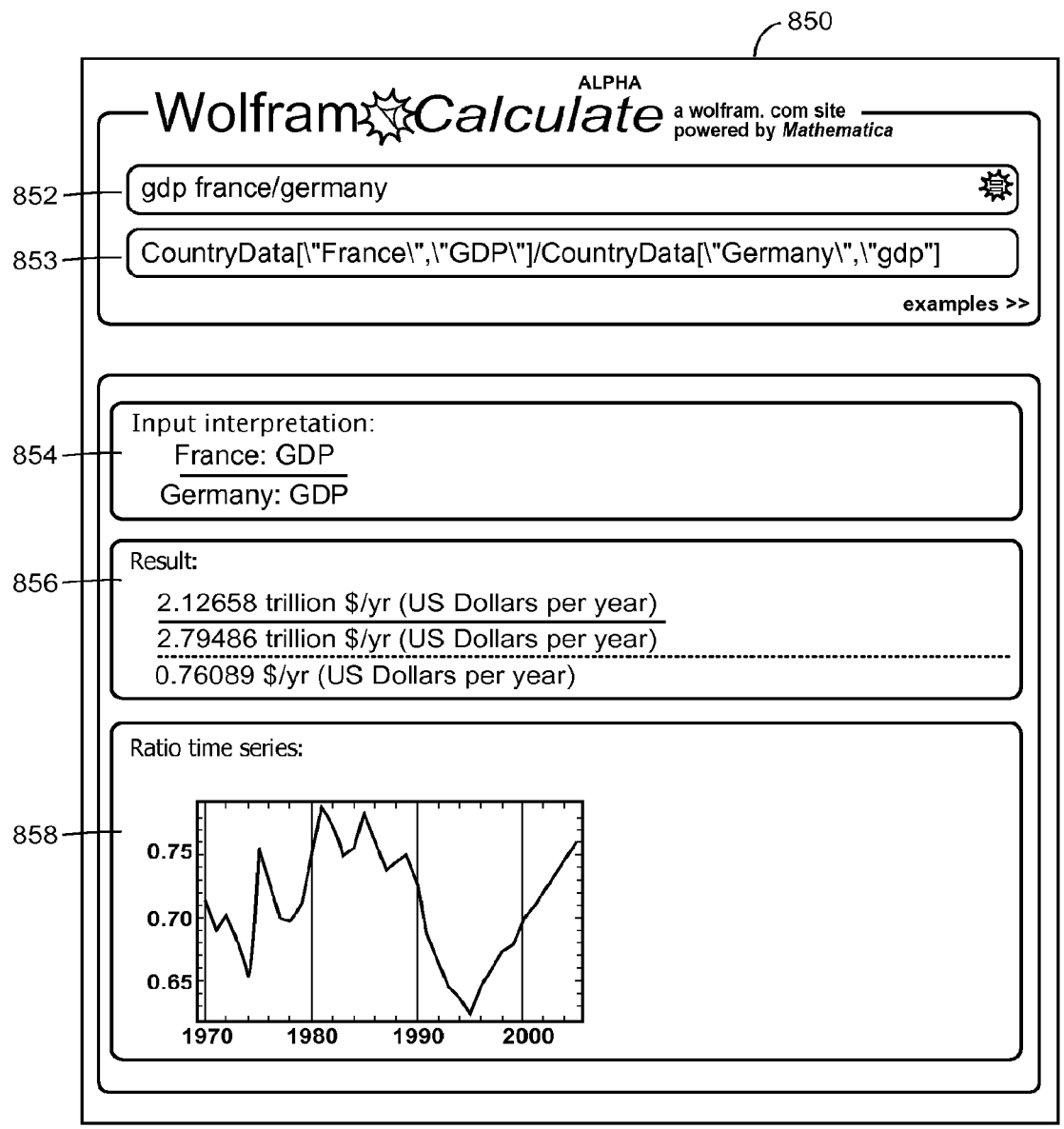
FIG. 17 is an illustration of still another example display that may be utilized in an implementation of the method of FIG. 1.

FIG. 17 is an illustration of a portion of another example display 850 that may be utilized in an implementation of a method such as the method 100 of FIG. 1. The portion of the display 850 may be displayed in response to a user entering the text "gdp France/Germany" in a portion 852 and activating a button on the display 850. The determined formula is an expression in a precise syntax and is displayed in a portion 853. The display 850 may display information related to the determined expression. For example, the display 850 may include various fields 854, 856, 858 that provide information related to the expression in the field 853. The field 854 provides a more "user friendly" indication of the determined formula. The field 856 includes an evaluation of the formula with data obtained from a database, for example. The field 858 includes a plot of an evaluation of the formula using GDP values from several years.

Figure 18:
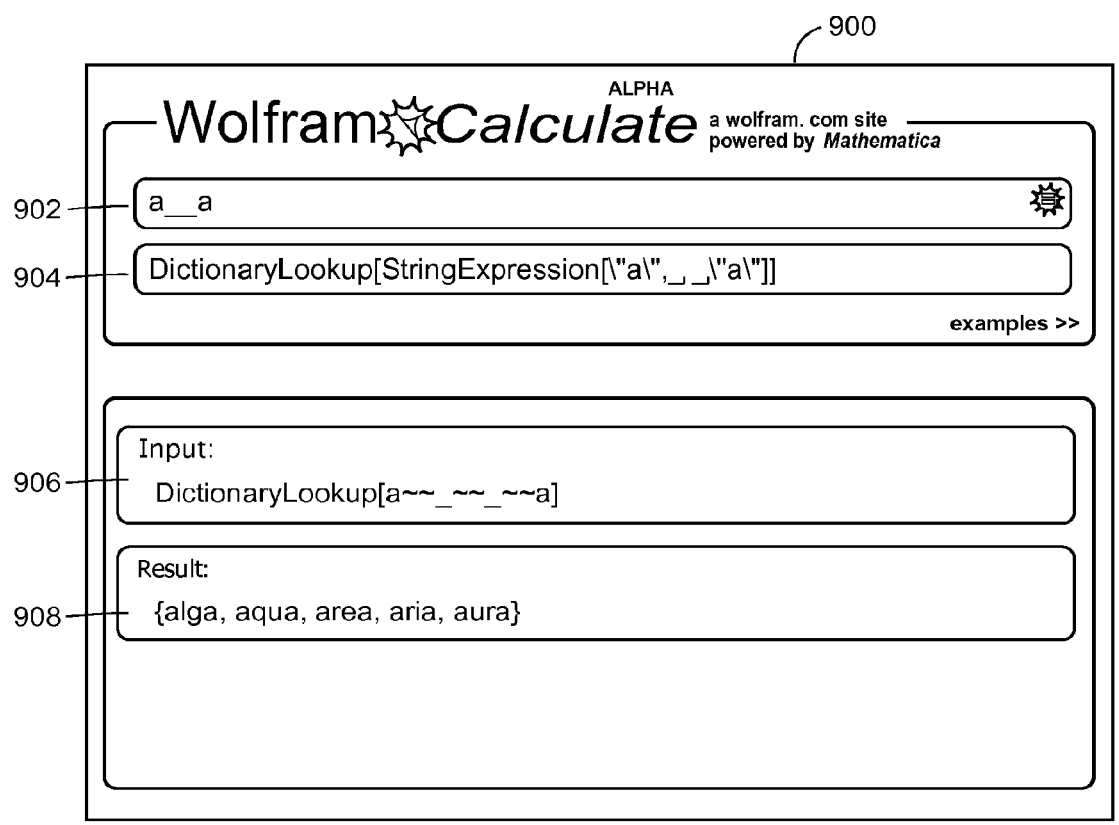
FIG. 18 is an illustration of another example display that may be utilized in an implementation of the method of FIG. 1.

FIG. 18 is an illustration of a portion of another example display 900 that may be utilized in an implementation of a method such as the method 100 of FIG. 1. The portion of the display 900 may be displayed in response to a user entering the text "a_a" in a field 902 and activating a button on the display 900. The determined formula is an expression in a precise syntax and is displayed in a portion 904. The display 900 may display information related to the determined expression. For example, the display 900 may include various fields 906 and 908 that provide information related to the expression in the field 904. The field 906 provides a more "user friendly" indication of the determined formula. The field 908 includes an evaluation of the formula with data obtained from a database, for example.

Figure 19:
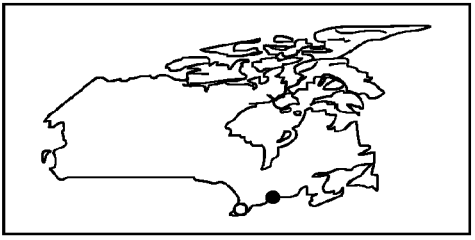
FIG. 19 is an illustration of yet another example display that may be utilized in an implementation of the method of FIG. 1.

FIG. 19 is an illustration of a portion of another example display 950 that may be utilized in an implementation of a method such as the method 100 of FIG. 1. The portion of the display 900 may be displayed in response to a user entering the text "London" in a field 952 and activating a button on the display 950. The display 950 may display information related to the determined formula. For example, the display 950 may include various fields 954, 956, 958, 960, and 962 that provide information related to the determined formula. The field 954 provides a "user friendly" indication of the determined formula. The field 956 provides an alternative representation or indication of the determined formula. The field 958 includes data related to the formula and obtained from a database, for example. The field 960 includes a map indicating the location of London, Ontario, Canada. The field 962 includes location data for London, Ontario, Canada, obtained from a database, for example.

In the above-described methods and systems, the user input could be received in a variety of ways. For example, the user input could include text entered via a keyboard, a keypad, a touch screen, etc., of a device such as a workstation, a desktop computer, a laptop computer, a tablet computer, a personal digital assistant (PDA), a cellular phone, etc. The user input could be received in other forms as well. For example, the user input could be received via a voice recognition system. As another example, the user input could be received in a graphical form. For instance, handwriting recognition techniques could be used to convert the input into a textual form or some other form.

Also, a user could draw a plot of a function on a touch screen of a computer. Formulas to generate the plot, or an approximation of the plot, could be determined. As another example, a user could also draw notations or annotations on the plot, and these notations or annotations could be utilized to determine formulas and/or to format output to be presented to the user. For instance, if a user draws a plot and puts an "X" at the maximum of a curve, a formula for determining the maximum of the function corresponding to the plot could be determined. Additionally or alternatively, if a plot of the determined formula is presented to the user, the presented plot could include an "X" or a similar mark in a location corresponding to the location of the "X" drawn by the user.

Additionally, the input need not be received directly from a user. For example, the methods and systems described above could receive input from a file, or the input could be a signal generated by a device such as a sensor, a signal received by another computing device, etc. For instance, a file or signal could include data values, and a function, a model, etc., that best fits the data could be determined.

In presenting the formulas, outputs, software programming code, etc., to a user, such information may be presented in a way that allows it to be readily transferred to a file such as document. For instance, a formula could be presented as text so that it could be transferred to another document using standard "cut and paste" techniques. Alternatively, the formulas, outputs, software programming code could be presented along with a mechanism that would allow such information to be inserted into another document having a particular format such as a spreadsheet, a word processing document for use with a particular equation editor, a MATHEMATICA® notebook, etc. The mechanism could include a user interface mechanism such as a button, a drag-and-drop mechanism, etc. For example, a user could activate a button to have an equation inserted into a word processing document, the equation being in a format of a particular equation editor compatible with the word processing program.

Any of the techniques described above, including the blocks described with reference to FIGS. 1-16, may be implemented using software comprising computer program instructions. Such computer program instructions may control the operation of a computing device such as a desktop computer, a laptop computer, a tablet computer, a workstation, a server, a mainframe, a cellular phone, a telephone, a set top box, a PDA, a pager, a processing system of an electronic toy, a processing system of an electronic game, a processing system of a consumer electronics device, etc. The computing device may have a memory in which the computer program instructions may be stored. The computer program instructions may be written in any high level language such as the programming language used with MATHEMATICA® software systems, C, C++, C#, Java or the like or any low-level assembly or machine language. By storing computer program instructions in a memory of the computing device, the computing device is physically and/or structurally configured in accordance with the computer program instructions.

While many methods and systems have been described herein as being implementable in software, they may be implemented in hardware, firmware, etc., and may be implemented by a variety of computing systems and devices. Thus, the method blocks and system blocks described herein may be implemented in a standard multi-purpose central processing unit (CPU), a special purpose CPU, or on specifically designed hardware or firmware such as an application-specific integrated circuit (ASIC) or other hard-wired device as desired. When implemented in software, the software routine may be stored in any computer readable memory such as on a magnetic disk, a laser disk (such as a compact disk (CD), a digital versatile disk (DVD)), a flash memory, a memory card, a memory stick, etc., or other storage medium, in a RAM or ROM of a computer or processor, in any database, etc. Likewise, this software may be delivered via any known or desired delivery method including, for example, on a computer readable memory or other transportable computer storage mechanism or over a communication channel such as a telephone line, the internet, etc. (which are viewed as being the same as or interchangeable with providing such software via a transportable storage medium).

The present disclosure has been described with reference to specific examples, which are intended to be illustrative only and not to be limiting. It will be apparent to those of ordinary skill in the art that changes, additions or deletions may be made to the disclosed examples without departing from the spirit and scope of the disclosure. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of this application.

Thus, many modifications and variations may be made in the techniques and systems described and illustrated herein without departing from the spirit and scope of the present invention. Accordingly, it should be understood that the methods and systems described herein are illustrative only and are not limiting upon the scope of the invention.

What is claimed is:

1. A computer-implemented method, comprising:
receiving, at one or more computer processors, a user input in an imprecise syntax, wherein:
the user input in the imprecise syntax includes at least (i) a word, or a phrase, that corresponds to a formula having a plurality of mathematical or scientific parameters, and (ii) one or more words, and/or one or more phrases, that correspond to one or more parameter values corresponding to the formula,
the user input in the imprecise syntax is expressed using natural language and/or informal terminology spoken by a user, and
the user input in the imprecise syntax corresponds to a digital representation of an audio signal corresponding to speech spoken by the user, the digital representation of the audio signal corresponding to the speech spoken by the user having been generated by a voice recognition system;
analyzing, at the one or more computer processors, the user input in the imprecise syntax to determine the formula with the one or more parameter values integrated into the formula;
calculating, at the one or more computer processors, a numerical result using the determined formula with the one or more parameter values integrated into the determined formula; and
generating, at the one or more computer processors, an output, using the numerical result, to perform a physical machine action.

2. The computer-implemented method of claim 1, wherein analyzing the user input in the imprecise syntax to determine the formula with the one or more parameter values integrated into the formula further comprises:
determining a plurality of possible formulas that correspond to the user input in the imprecise syntax; and
at least one of (i) ranking the plurality of possible formulas, and (ii) eliminating one or more possible formulas of the plurality of possible formulas.

3. The computer-implemented method of claim 1, wherein analyzing the user input in the imprecise syntax to determine the formula with the one or more parameter values integrated into the formula further comprises:
analyzing the user input in the imprecise syntax to identify a first parameter corresponding to a first parameter value in the one or more parameter values; and
determining the formula based, at least in part, on the identified first parameter.

4. The computer-implemented method of claim 1, wherein analyzing the user input in the imprecise syntax to determine the formula with the one or more parameter values integrated into the formula further comprises:
identifying the formula from the user input in the imprecise syntax at least by:
parsing the user input in the imprecise syntax into a plurality of tokens,
re-arranging the plurality of tokens into a plurality of expressions in a precise syntax, and
analyzing the plurality of expressions in the precise syntax.

5. The computer-implemented method of claim 1, wherein analyzing the user input in the imprecise syntax to determine the formula with the one or more parameter values integrated into the formula further comprises:
partitioning the user input in the imprecise syntax into a plurality of tokens, wherein each token of the plurality of tokens comprises a word, a phrase, or a numerical expression;
generating one or more expressions in a precise syntax using the plurality of tokens; and
providing the one or more expressions in the precise syntax to a plurality of modules, wherein each module of the plurality of modules is configured to at least one of i) determine formulas corresponding to a respective subject matter category, among a plurality of different subject matter categories of formulas, by analyzing the one or more expressions in the precise syntax provided to the module, and ii) evaluate formulas corresponding to the respective subject matter category, and wherein each module of the plurality of modules is implemented using software executed by the one or more computer processors.

6. The computer-implemented method of claim 5, wherein analyzing the user input in the imprecise syntax to determine the formula with the one or more parameter values integrated into the formula further comprises:
for each module of the plurality of modules, providing an output of the module as one or more inputs to one or more other modules of the plurality of modules.

7. The computer-implemented method of claim 1, wherein analyzing the user input in the imprecise syntax to determine the formula with the one or more parameter values integrated into the formula further comprises:
analyzing the user input in the imprecise syntax to determine a correspondence between (i) the one or more parameter values corresponding to the user input in the imprecise syntax and (ii) one or more mathematical or scientific parameters of the formula.

8. The computer-implemented method of claim 1, further comprising:
determining, at the one or more computer processors, that one or more additional parameter values are required to calculate the numerical result; and
electronically prompting, at the one or more computer processors, the user to provide additional information corresponding to the one or more additional parameter values.

9. The computer-implemented method of claim 1, wherein generating the output, using the numerical result, to perform the physical machine action further comprises displaying the numerical result on a display device.

10. The computer-implemented method of claim 1, wherein generating the output, using the numerical result, to perform the physical machine action further comprises electronically inserting the numerical result into an electronic document.

11. The computer-implemented method of claim 1, wherein generating the output, using the numerical result, to perform the physical machine action further comprises transmitting the numerical result to a computing device via a communication network.

12. The computer-implemented method of claim 1, wherein generating the output, using the numerical result, to perform the physical machine action further comprises sending the numerical result to a software application being executed by the one or more computer processors.

13. The computer-implemented method of claim 1, wherein generating the output, using the numerical result, to perform the physical machine action further comprises generating an audio signal indicative of the numerical result.

14. The computer-implemented method of claim 1, wherein generating the output, using the numerical result, to perform the physical machine action further comprises using the numerical result to control a motor.

15. The computer-implemented method of claim 1, wherein generating the output, using the numerical result, to perform the physical machine action further comprises using the numerical result to control a light.

16. The computer-implemented method of claim 1, further comprising:
displaying, at the one or more computer processors, on a display device, a graphical user interface mechanism for facilitating adjustment, by the user, of one or more mathematical or scientific parameters of the formula.

17. The computer-implemented method of claim 1, further comprising:
receiving, at the one or more computer processors, one or more respective indications of one or more respective adjustments of one or more respective parameter values corresponding to the formula;
calculating, at the one or more computer processors, an updated numerical result using i) the determined formula and ii) the one or more respective adjustments of the one or more respective parameter values corresponding to the formula; and
using, at the one or more computer processors, the updated numerical result to perform a subsequent physical machine action.

18. The computer-implemented method of claim 17, wherein receiving the one or more respective indications of the one or more respective adjustments of the one or more respective parameter values corresponding to the formula further comprises:
receiving a first indication of a first adjustment of a first parameter value corresponding to the formula;
wherein the first indication of the first adjustment of the first parameter value corresponding to the formula corresponds to a digital representation of an audio signal corresponding to subsequent speech spoken by the user, the digital representation of the audio signal corresponding to the subsequent speech spoken by the user having been generated by the voice recognition system.

19. The computer-implemented method of claim 17, wherein receiving the one or more respective indications of the one or more respective adjustments of the one or more respective parameter values corresponding to the formula further comprises:
receiving a first indication of a first adjustment of a first parameter value corresponding to the formula via a graphical user interface mechanism displayed on a display device.

20. The computer-implemented method of claim 17, wherein receiving the one or more respective indications of the one or more respective adjustments of the one or more respective parameter values corresponding to the formula further comprises:
receiving a first indication of a first adjustment of a first parameter value corresponding to the formula via a mechanical user interface device.

21. A system, comprising:
one or more memory devices; and
one or more processors coupled to the one or more memory devices;
wherein the one or more memory devices store machine readable instructions that, when executed by the one or more processors, cause the one or more processors to:
receive a user input in an imprecise syntax, wherein:
the user input in the imprecise syntax includes at least (i) word, or a phrase, that corresponds to a formula having a plurality of mathematical or scientific parameters, and (ii) one or more words, and/or one or more phrases, that correspond to one or more parameter values corresponding to the formula,
the user input in the imprecise syntax is expressed using natural language and/or informal terminology spoken by a user, and
the user input in the imprecise syntax corresponds to a digital representation of an audio signal corresponding to speech spoken by the user, the digital representation of the audio signal corresponding to the speech spoken by the user having been generated by a voice recognition system;
wherein the one or more memory devices store further machine readable instructions that, when executed by the one or more processors, cause the one or more processors to:
analyze the user input in the imprecise syntax to determine the formula with the one or more parameter values integrated into the formula;
calculate a numerical result using the determined formula with the one or more parameter values integrated into the determined formula; and
generate an output, using the numerical result, to perform a physical machine action.

22. The system of claim 21, wherein the one or more memory devices store further machine readable instructions that, when executed by the one or more processors, cause the one or more processors to:
determine a plurality of possible formulas that correspond to the user input in the imprecise syntax; and
at least one of (i) ranking the plurality of possible formulas, and (ii) eliminating one or more possible formulas of the plurality of possible formulas.

23. The system of claim 21, wherein the one or more memory devices store further machine readable instructions that, when executed by the one or more processors, cause the one or more processors to:
identify the formula from the user input in the imprecise syntax at least by:
parsing the user input in the imprecise syntax into a plurality of tokens,
re-arranging the plurality of tokens into a plurality of expressions in a precise syntax, and
analyzing the plurality of expressions in the precise syntax.

24. The system of claim 21, wherein the one or more memory devices store further machine readable instructions that, when executed by the one or more processors, cause the one or more processors to:
partition the user input in the imprecise syntax into a plurality of tokens, wherein each token of the plurality of tokens comprises a word, a phrase, or a numerical expression;
generate one or more expressions in a precise syntax using the plurality of tokens; and
provide the one or more expressions in the precise syntax to a plurality of modules, wherein each module of the plurality of modules is configured to at least one of i) determine formulas corresponding to a respective subject matter category, among a plurality of different subject matter categories of formulas, by analyzing the one or more expressions in the precise syntax provided to the module, and ii) evaluate formulas corresponding to the respective subject matter category, and wherein each module of the plurality of modules is implemented using machine readable instructions, stored in the one or more memory devices, that are executed by the one or more processors.

25. The system of claim 24, wherein the one or more memory devices store further machine readable instructions that, when executed by the one or more processors, cause the one or more processors to:
for each module of the plurality of modules, provide an output of the module as one or more inputs to one or more other modules of the plurality of modules.

26. The system of claim 21, wherein the one or more memory devices store further machine readable instructions that, when executed by the one or more processors, cause the one or more processors to:
analyze the user input in the imprecise syntax to determine a correspondence between (i) the one or more parameter values corresponding to the user input in the imprecise syntax and (ii) one or more mathematical or scientific parameters of the formula.

27. The system of claim 21, wherein the one or more memory devices store further machine readable instructions that, when executed by the one or more processors, cause the one or more processors to:
determine that one or more additional parameter values are required to calculate the numerical result; and
electronically prompt the user to provide additional information corresponding to the one or more additional parameter values.

28. The system of claim 21, further comprising:
a display device coupled to the one or more processors;
wherein the one or more memory devices store further machine readable instructions that, when executed by the one or more processors, cause the one or more processors to display the numerical result on the display device.

29. The system of claim 28, wherein the one or more memory devices store further machine readable instructions that, when executed by the one or more processors, cause the one or more processors to:
display, on the display device, a graphical user interface mechanism for facilitating adjustment, by the user, of one or more mathematical or scientific parameters of the formula.

30. The system of claim 21, wherein the one or more memory devices store further machine readable instructions that, when executed by the one or more processors, cause the one or more processors to:
electronically insert the numerical result into an electronic document.

31. The system of claim 21, wherein the one or more memory devices store further machine readable instructions that, when executed by the one or more processors, cause the one or more processors to:
transmit the numerical result to a computing device via a communication network.

32. The system of claim 21, wherein the one or more memory devices store further machine readable instructions that, when executed by the one or more processors, cause the one or more processors to:
send the numerical result to a software application being executed by the one or more processors.

33. The system of claim 21, wherein the one or more memory devices store further machine readable instructions that, when executed by the one or more processors, cause the one or more processors to:
use the numerical result to generate an audio signal.

34. The system of claim 21, wherein the one or more memory devices store further machine readable instructions that, when executed by the one or more processors, cause the one or more processors to:
use the numerical result to control a motor.

35. The system of claim 21, wherein the one or more memory devices store further machine readable instructions that, when executed by the one or more processors, cause the one or more processors to:
use the numerical result to control a light.

36. The system of claim 21, wherein the one or more memory devices store further machine readable instructions that, when executed by the one or more processors, cause the one or more processors to:
receive one or more respective indications of one or more respective adjustments of one or more respective parameter values corresponding to the formula;
calculate an updated numerical result using i) the determined formula and ii) the one or more respective adjustments of the one or more respective parameter values corresponding to the formula; and
use the updated numerical result to perform a subsequent physical machine action.

37. The system of claim 36, wherein the one or more memory devices store further machine readable instructions that, when executed by the one or more processors, cause the one or more processors to:
receive a first indication of a first adjustment of a first parameter value corresponding to the formula;
wherein the first indication of the first adjustment of the first parameter value corresponding to the formula corresponds to a digital representation of an audio signal corresponding to subsequent speech spoken by the user, the digital representation of the audio signal corresponding to the subsequent speech spoken by the user having been generated by the voice recognition system.

38. The system of claim 36, further comprising:
a display device coupled to the one or more processors;
wherein the one or more memory devices store further machine readable instructions that, when executed by the one or more processors, cause the one or more processors to:
receive a first indication of a first adjustment of a first parameter value corresponding to the formula via a graphical user interface mechanism displayed on the display device.

39. The system of claim 36, further comprising:
a mechanical user interface device;
wherein the one or more memory devices store further machine readable instructions that, when executed by the one or more processors, cause the one or more processors to:
receive a first indication of a first adjustment of a first parameter value corresponding to the formula via the mechanical user interface device.

40. The system of claim 21, further comprising:
the voice recognition system, coupled to the one or more processors.

* * * * *